United States Patent [19]
Stoughton et al.

[11] Patent Number: 6,132,969
[45] Date of Patent: Oct. 17, 2000

[54] METHODS FOR TESTING BIOLOGICAL NETWORK MODELS

[75] Inventors: Roland Stoughton, San Diego, Calif.; Richard M. Karp, Seattle, Wash.

[73] Assignee: Rosetta Inpharmatics, Inc., Kirkland, Wash.

[21] Appl. No.: 09/099,722

[22] Filed: Jun. 19, 1998

[51] Int. Cl.$^7$ .............................. C12Q 1/68; C12Q 1/00; G01N 33/53; G06F 17/00

[52] U.S. Cl. .................................. 435/6; 435/4; 435/7.1; 364/400

[58] Field of Search ..................... 435/4, 6, 7.1; 364/400

[56] References Cited

U.S. PATENT DOCUMENTS

| | | |
|---|---|---|
| 5,445,934 | 8/1995 | Fodor et al. . |
| 5,569,588 | 10/1996 | Ashby et al. . |
| 5,645,988 | 7/1997 | Vande Woude et al. . |
| 5,744,305 | 4/1998 | Fodor et al. . |
| 5,777,888 | 7/1998 | Rine et al. . |
| 5,800,992 | 9/1998 | Fodor et al. . |
| 5,811,231 | 9/1998 | Farr et al. . |

FOREIGN PATENT DOCUMENTS

| | | |
|---|---|---|
| 0 816 511 A1 | 1/1996 | European Pat. Off. . |
| WO 94/17208 | 8/1994 | WIPO . |
| WO 97/10365 | 3/1997 | WIPO . |
| WO 97/27317 | 7/1997 | WIPO . |
| WO 98/06874 | 2/1998 | WIPO . |

OTHER PUBLICATIONS

Pompon et al. Genetically engineered yeast cells and their applications. Toxicology Lett. vol. 82/83 pp. 815–822, 1995.

Lemieux et al. Simulation of the voltage dependence of the Na, K pump applied to cardiac cells. J. Theoretical Biol. vol. 150 pp. 73–91, 1991.

Urien MicroPharm–K, a microcomputer interactive program for the analysis and simulation of pharmacokinetic processes. Pharmaceutical res. vol. 12 pp. 1225–1230, 1995.

Kuijpers et al. Membrane surface antigen expression on neutrophils: A reappraisal of the use of surface markers for neutrophil activation. Blood vol. 78 pp. 1105–1111, 1991.

Adams et al. Two–dimensional gel electrophoresis using the O'Farrell system. Unit 10.4, pp. 10.4.1–10.4.13 in Current Protocols in Molecular Biology, Ausubel et al. Eds. John Wiley & Sons, 1992.

Uhlman et al. Antisense oligonucleotides: A new therapeutic principle. Chemical Reviews vol. 90 pp. 543–584, 1990.

Anderson et al., 1994, "Involvement of the protein tyrosine kinase p56$^{lck}$ in T cell signalling and thymocyte development", Adv. Immunol. 56:151–178.

Baudin et al., 1993, "A simple and efficient method for direct gene deletion in Saccharomyces cerevisiae", Nucl. Acids Res. 21:3329–3330.

Belshaw et al., 1996, "Controlling protein association and subcellular localization with a synthetic ligand that induces heterodimerization of proteins", Proc. Natl. Acad. Sci. USA 93:4604–4607.

Biocca, 1995, "Intracellular immunization: antibody targeting to subcellular compartments", Trends in Cell Biology 5:248–253.

Blanchard et al., 1996, "Sequence to array: probing the genome's secrets", Nature Biotechnology 14:1649.

Blanchard et al., 1996, "High–density oligonucleotide arrays", Biosensors & Bioelectronics 11:687–690.

Chee et al., 1996, "Accessing genetic information with high–density DNA arrays", Science 274:610–614.

Cotten and Birnstiel, 1989, "Ribozyme mediated destruction of RNA in vivo", EMBO J. 8:3861–3866.

Mutants, Science 63:1273–1276.

Gari et al., 1997, "A set of vectors with a tetracycline regulatable promoter system for modulated gene expression in Saccharomyces cravisiae", Yeast 13:837–848.

Goffreau et al., 1996, "Life with 6000 genes", Science 274:546–567.

Gossen and Bujard, 1992, "Tight control of genes expression in mammalian cells by tetracycline–responsive promoters", Proc. Natl. Acad. Sci. USA 89:5547–5551.

Gossen et al., 1995, "Transcriptional activation by tetracyclines in mammalian cells" Science 268:1766–1769.

Guo et al., 1994, "Direct fluorescence analysis of genetic polymorphisms by hybridization with oligonucleotide arrays on glass supports", Nucl. Acids Res. 22:5456–5465.

Hanke et al., 1996, "Discovery of a novel, potent, and Src family–selective tyrosine kinase inhibitor", J. Biol. Chem. 271:695–701.

(List continued on next page.)

*Primary Examiner*—John S. Brusca
*Attorney, Agent, or Firm*—Pennie & Edmonds LLP

[57] ABSTRACT

The present invention provides methods and systems for testing and confirming how well a network model represents a biological pathway in a biological system. The network model comprises a network of logical operators relating input cellular constituents (e.g., mRNA or protein abundances) to output classes of cellular constituents, which are affected by the pathway in the biological system. The methods of this invention provide, first, for choosing complete and efficient experiments for testing the network model which compare relative changes in the biological system in response to perturbations of the network. The methods also provide for determining an overall goodness of fit of the network model to biological system by: predicting from the network model how output classes behave in response to the chosen experiments, finding measures of relative change of cellular constituents actually observed in the chosen experiments, finding goodnesses of fit of each observed cellular constituent to an output class with which the cellular constituent has the strongest correlation, and determining an overall goodness of fit of the network model from the individual goodnesses of fit of each observed cellular constituent. Additionally, these methods provide for testing the significance of the overall goodness of fit according to a nonparametric statistical test using an empirically determined distribution of possible goodnesses of fit. This invention also provides for computer systems for carrying out the computational steps of these methods.

65 Claims, 12 Drawing Sheets

OTHER PUBLICATIONS

Hartwell et al., 1997, "Integrating genetic approaches into the discovery of anticancer drugs", Science 278:1064–1068.

Hayden et al., 1997, "Antibody engineering", Curr. Opin. Immunol. 9:201–212.

Herskowitz, 1987, "Functional inactivation of genes by dominant negative mutations", Nature 329:219–222.

Hoffmann et al., 1997, "A novel tetracycline–dependent expression vector with low basal expression and potent regulatory properties in various mammalian cell lines" Nucl. Acids Res. 25: 1078–1079.

Johnston and Davis, 1984, "Sequences that regulate the divergent GAL1–GAL10 promoter in Saccharomyces cerevisiae", Mol. Cell. Biol. 4:1440–1448.

Kerjan et al., 1986, "Nucleotide sequence of Saccharomyces cerevisiae MET25 gene", Nucl. Acids Res. 14:7861–7871.

Lander, 1996, "The new genomics: Global views of biology", Science 274:536–539.

Lennon and Lehrach, 1991, "Hybridization analyses of arrayed cDNA libraries" TIG 7:314–317.

Mascorro–Gallardo et al., 1996, "Construction of a CUP1 promoter–based vector to modulate gene expression in Saccharomyces cerevisiae", Gene 172:169–170.

Matheos et al., 1997, "Tcn1p/Crz1p, a calcineurin–dependent transcription factor that differentially regulates gene expression in Saccharomyces cerevisiae", Genes & Dev. 11:3445–3458.

McAdams and Shapiro, 1995, "Circuit simulation of genetic networks", Science 269:650–656.

Mikulecky, 1990, "Modeling intestinal absorption and other nutrition–related processes using PSPICE and STELLA", J. Ped. Gastroenterol. Nutr. 11:7–20.

Mounts and Liebman, 1997, "Qualitative modeling of normal blood coagulation and its pathological states using stochastic activity networks", Int. J. Biol. Macromolecules 20:265–281.

Murmberg et al., 1994, "Regulatable promoters of Saccharomyces cerevisiae: Comparison of transcriptional activity and their use for heterologous expression", Nucl. Acids. Res. 22:5767–5768.

Nguyen et al., 1995, "Differential gene expression in the murine thymus assayed by quantitative hybridization of arrayed cDNA clones", Genomics 29:207–216.

No et al., 1996, "Ecdysone–inducible gene expression in mammalian cells and transgenic mice", Proc. Natl. Acad. Sci. USA 93:3346–3351.

murine c–kit/white otting locus: $W_{37}$, $W^v$, $W^{41}$ and W, EMBO 9:1805–1813.

Oliff and Friend, 1997, "Cancer, principles & practice of oncology, molecular targets for drug development", Mol. Pharmacol. 68:3115–3125.

Perlmutter and Alberola–IIa, 1996, "The use of dominant–negative mutations to elucidate signal transduction pathways in lymphocytes", Curr. Opin. Immunol. 8:285–290.

Polyak et al., 1997, "A model for p53–induced apoptosis", Nature 389:300–306.

Reinitz and Sharp, 1995, "Mechanism of eve stripe formation", Mech. Dev. 49:133–158.

Schena, 1996, "Genome analysis with gene expression microarrays", BioEssays 18:427.

Schena et al., 1996, "Parallel human genome analysis: microarray–based expression monitoring of 1000 genes", Proc. Natl. Acad. Sci. USA 93:10614–10619.

Schena et al., 1995, "Quantitative monitoring of gene expression patterns with a complementary DNA microarray", Science 270:467–470.

Shalon et al., 1996, "A DNA microarray system for analyzing complex DNA samples using two–color fluorescent probe hybridization", Genome Research 639–645.

Shiue, 1997, "Identification of candidate genes for drug discovery by differential display", Drug Dev. Res. 41:142–159.

Shoemaker et al., 1996, "Quantitative phenotypic analysis of yeast deletion mutants using a highly parellel molecular bar–coding strategy", Nature Genetics 14:450–456.

Southern, 1996, "DNA chips: analysing sequence by hybridization to oligonucleotides on a large scale", TIG 12:110–115.

Spencer, 1996, "Creating conditional mutations in mammals", TIG 12:181–187.

Stathopoulos and Cyert,,, 1997, "Calcineurin acts through the CRZ1/TCN1–encoded transcription factor to regulate gene expression in yeast", Genes & Dev. 11:3432–3444.

Straus and Weiss, 1992, "Genetic evidence for the involvement of the lck tyrosine kinase in signal transduction through the T cell antigen receptor", Cell 70:585–593.

Thomas et al., 1995, "Dynamical behaviour of biological regulatory networs—I. Biological role of feedback loops and practical use of the concept of the loop–characteristic state", Bull. Math. Biol. 57:247–276.

Yuh et al., 1998, "Genomic Cis–regulatory logic: experimental and computational analysis of a sea urchin gene", Science 279:1896–1902.

Velculescu et al., 1995, "Serial analysis of gene expression", Science 270:484–487.

Zhao et al., 1995, "High–density cDNA filter analysis: a novel approach for large–scale, quantitative analysis of gene expression", Gene 156:207–213.

———• POSITIVE INPUT
———⊣ NEGATIVE INPUT

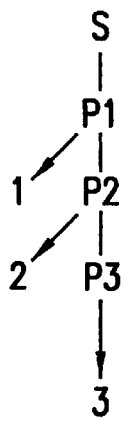
FIG. 3A
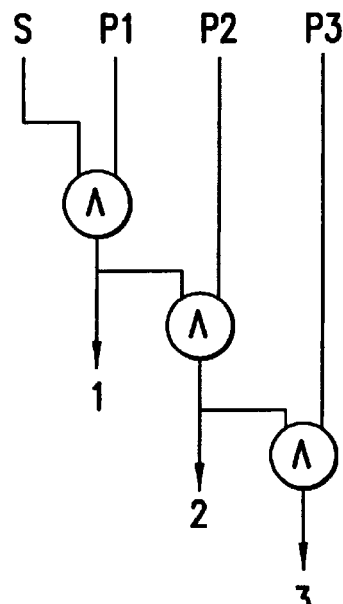
FIG. 3B
CLASS 1 = S ∧ P1
CLASS 2 = S ∧ P1 ∧ P2
CLASS 3 = A ∧ P1 ∧ P2 ∧ P3
FIG. 3C

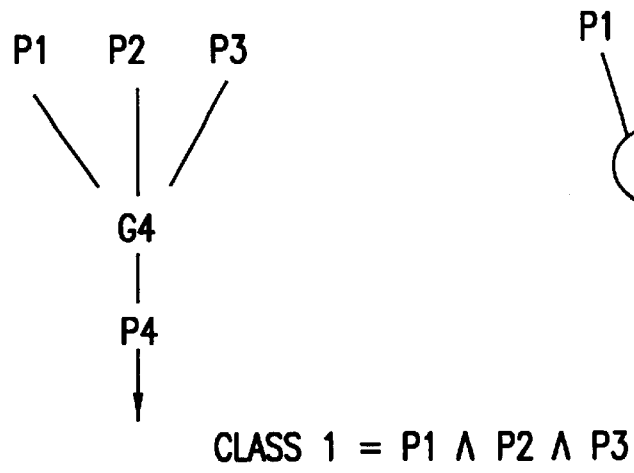
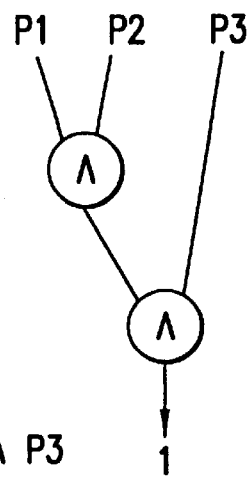
CLASS 1 = P1 ∧ P2 ∧ P3
FIG. 4A            FIG. 4B
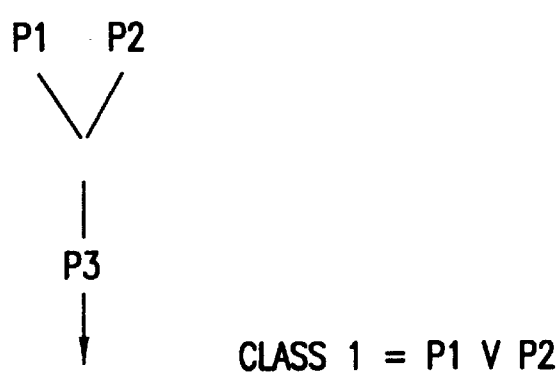
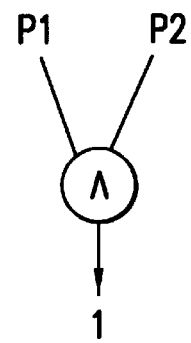
CLASS 1 = P1 ∨ P2
FIG. 5A            FIG. 5B
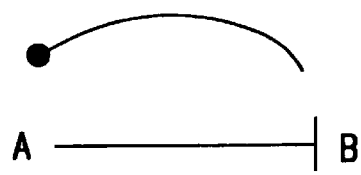
FIG. 6

| CLASS | WT vs. WT | +/- cna | +/- cph | +/- fpr | +/- FK506 | +/- FK506 (-cna) | +/- FK506 (-cph) | +/- FK506 (-fpr) | +/- Cyc A | +/- Cyc A (-cna) | +/- Cyc A (-cph) | +/- Cyc A (-fpr) |
|---|---|---|---|---|---|---|---|---|---|---|---|---|
| 1 | 0 | 0 | 0 | 0 | -1 | -1 | -1 | -1 | 0 | 0 | 0 | 0 |
| 2 | 0 | 0 | 0 | -1 | -1 | -1 | -1 | 0 | 0 | 0 | 0 | 0 |
| 3 | 0 | 0 | 0 | 0 | -1 | 0 | -1 | 0 | 0 | 0 | 0 | 0 |
| 4 | 0 | -1 | 0 | 0 | 0 | 0 | 0 | 0 | -1 | -1 | 0 | -1 |
| 5 | 0 | 0 | -1 | 0 | 0 | 0 | 0 | 0 | -1 | -1 | 0 | -1 |
| 6 | 0 | 0 | 0 | 0 | 0 | 0 | 0 | 0 | -1 | -1 | 0 | -1 |
| 7 | 0 | 0 | 0 | 0 | 0 | 0 | 0 | 0 | 0 | 0 | -1 | -1 |

FIG. 7B

METHODS FOR TESTING BIOLOGICAL NETWORK MODELS

1. FIELD OF THE INVENTION

The field of this invention relates to methods and systems for determination of biological pathways and particularly for the testing and confirmation of network models of biological pathways.

2. BACKGROUND

A biological system such as a yeast or mammalian cell is an immensely complicated set of interacting pathways involving environmental inputs, protein interactions, gene regulations, and so forth. Improved knowledge concerning these pathways would be of immense importance in many scientific and technological fields.

For but one example, identification or improved knowledge of the biological pathway(s) of action of a drug or drug candidate would be of great commercial and human importance. Although the primary molecular target of and cellular pathways affected by a drug are often known or suspected because the drug was originally selected by a specific drug screen, it is important to verify its action on such a primary pathway and to quantify its action along other secondary pathways which may be harmful, or may be beneficial, often in unsuspected ways. In other cases, such as in drug discovery, the primary pathways of action of a candidate drug are unknown, and these must be determined.

Drug discovery, a critical step in the development of treatments for human diseases, is presently dominated by two approaches neither of which directly provide information on the pathways of action of a drug candidate. A first approach begins with a screen for compounds that have a desired effect on a cell (e.g., induction of apoptosis), or organism (e.g., inhibition of angiogenesis) as measured in a specific biological assay. Compounds with the desired activity may then be modified to increase potency, stability, or other properties, and the modified compounds retested in the assay. This approach returns little or no information on the mechanisms of action or cellular pathways affected by the candidates.

A second approach to drug discovery involves testing numerous compounds for a specific effect on a known molecular target, typically a cloned gene sequence or an isolated enzyme or protein. For example, high-throughput assays can be developed in which numerous compounds can be tested for the ability to change the level of transcription from a specific promoter or the binding of identified proteins. Although the use of high-throughput screens is a powerful methodology for identifying drug candidates, again it provides little or no information about the effects of a compound at the cellular or organismal level, in particular information concerning the actual cellular pathways affected.

In fact, analysis of the pathway of efficacy and toxicity of candidate drugs can consume a significant fraction of the drug development process (see, e.g., Oliff et al., 1997, "Molecular Targets for Drug Development," in DeVita et al. Cancer: Principles & Practice of Oncology 5th Ed. 1997 Lippincott-Raven Publishers, Philadelphia). Therefore, methods of improving this analysis are of considerable current value.

In the past, it has been possible to glean some information to some extent about the pathways and mechanisms occurring inside a biological system of interest (including pathways of drug action) by simply observing the system's response to known inputs. The response observed has typically been gene expressions (i.e., mRNA abundances) and/or protein abundances. The inputs are experimental perturbations including genetic mutations (such as genetic deletions), drug treatments, and changes in environmental growth conditions.

However, it has been a usually hopeless task to try to infer the details of the system simply from the observed input-output relationships. Even if a pathway hypothesis is available, it has not been easy to determine if differential experiments provides adequate or efficient tests or confirmation of the pathway hypothesis. And even with such experiments, it has not always been known how to interpret their results in view of the pathway hypothesis.

Despite much effort and elaborate measurements, little concrete progress has been made in reconstructing the pathways of biological systems, much less their time-dependent interactions, from simple observations such as protein and mRNA concentrations (McAdams et al., 1995, Circuit simulation of genetic networks, Science 269:650–656; Reinitz et al., 1995, Mechanism of eve stripe formation, Mechanisms of Development 49:133–158).

One approach to this problem has been bringing modeling tools from other disciplines to bear on this problem. For example, boolean representations and network models familiar to the electrical engineering community have been applied to biological systems (Mikulecky, 1990, Modeling intestinal absorption and other nutrition-related processes using PSPICE and STELLA, J. of Ped. Gastroenterology and Nutrition 11:7–20; McAdams et al., 1995, Circuit simulation of genetic networks, Science 269:650–656). One application has been to the control of gene transcription during development, particularly during sequential organism development (Yuh et al., 1998, Genomic Cis-regulatory logic: Experimental and computational analysis of a sea urchin gene, Science 279:1896–1902).

The difficulties noted in developing and testing models of biological pathways in organisms has hindered effective use of the great advances recently made in biological measurement techniques.

These include recent advances in measuring gene transcription (Schena et al., 1995, Quantitative monitoring of gene expression patterns with a complementary DNA microarray, Science 270: 467–470; Lockhort et al., 1996, Expression monitoring by hybridization to high-density oligonucleotide arrays, Nature Biotechnology 14:1675–1680; Blanchard et al., 1996, Sequence to array: Probing the genome's secrets, Nature Biotechnology 14, 1649; U.S. Pat. No. 5,569,588, issued Oct. 29, 1996 to Ashby et al. for Methods for Drug Screening) and measuring protein abundances (McCormack et al., 1997, Direct analysis and identification of proteins in mixtures by LC,MS,MS and database searching at the low-femtomole level, Anal. Chem. 69(4):767–776; Chait, Trawling for proteins in the post-genome era, Nature Biotechnology 14:1544). Further technical advances have been made in the ability to modify and perturb biological systems, especially with individual genetic mutations throughout the genome (Mortensen et al., 1992, Production of homozygous mutant ES cells with a single targeting construct, Mol. Cell. Biol. 12:2391–2395; Wach et al., 1994, New heterologous modules for classical or PCR-based gene disruptions in *Saccharomyces cerevisiae*, Yeast 10:1793–1808). And of course, if quantitative methods were available, the rapid increase in computing power available per unit cost would make their exploitation ever more cost effective.

3. SUMMARY OF THE INVENTION

Accordingly, it is an object of the present invention to solve the problems present in the prior art by providing methods and systems for the quantitative testing and confirmation of network models of biological pathways which exploit the powerful gene expression measurement methods and cellular perturbation techniques now available.

The methods and systems of this invention are based in part on the discovery that a carefully selected group of strategic simplifications and abstractions of the problem as actually present permits useful and significant conclusions to be rapidly and easily obtained. One important abstraction involves coarsening the inputs and outputs of a network model to binary values and modeling interactions among cellular constituents in a biological system as logical gates with simple rules of combination. One important simplification involves testing and confirming a network model against experiments which compare relative changes between two states in a biological system instead of examining the absolute amounts in a single state. A further important simplification involves assessing the significance of a network model in view of experimental data by using an empirically derived probability distribution for rejecting a null hypothesis that the network model has no relation to the biological system.

In more detail, the present invention provides methods and systems for testing and confirming how well a network model represents a biological pathway in a biological system. The network model comprises a network of logical operators relating input cellular constituents (e.g., mRNA or protein abundances or activities) to output classes of cellular constituents, which are affected by the pathway in the biological system. The methods of this invention provide, first, for choosing complete and efficient experiments for testing the network model which compare relative changes in the biological system in response to perturbations of the network. The methods also provide for determining an overall goodness of fit of the network model to biological system by predicting from the network model how output classes behave in response to the chosen experiments, finding measures of relative change of cellular constituents actually observed in the chosen experiments, finding a goodness of fit of each observed cellular constituent to the output class with which the cellular constituent has the strongest correlation, and determining an overall goodness of fit of the network model from the individual goodness of fit of each observed cellular constituent. Additionally, these methods provide for testing the significance of the overall goodness of fit according to a nonparametric statistical test using an empirically determined distribution of possible goodness of fit. This invention also provides computer systems for carrying out the computational steps of these methods.

Additionally, the present invention has the following aspects. The methods of this invention also provide for performing iterative refinement of network models so that by starting from models with limited connections more complete and significant models can be refined.

The complete and efficient experiments can be routinely and automatically chosen from the formulation of the network model as a set of logical relations between input states and output classes. If costs are assigned to the types of experiments, such as might be related to laboratory effort or reagents cost, the experiment test can be chosen to minimize overall cost.

Even with the simplifications preferred, the goodness of fit determined for the network model typically has experimental errors whose statistical behavior is difficult or impossible to model analytically. Therefore, the methods of this invention preferably perform numerical randomizations of the observed data in order to obtain an empirical probability distribution for the goodness of fit of any model to the data.

In a first embodiment, the present invention provides a method for testing a network model of a biological system comprising (a) determining how well each of a plurality of measured relative changes matches each of a plurality of defined relative changes, wherein said defined relative changes are provided by a normalized influence matrix for a network model; (b) assigning each cellular constituent to a particular output class in the network model, wherein each cellular constituent is assigned to the output class having the defined relative change which best matches the measured relative change of that cellular constituent; and (c) determining an overall goodness of fit of data from network testing experiments (i.e., of measured relative changes for one or more cellular constituents), whereby said network model is tested or confirmed by said overall goodness of fit.

The network model of this first embodiment comprises: (i) a plurality of input constituents, wherein perturbations of one or more input constituents comprise input states; (ii) a plurality of output classes of behaviors associated with output states; and (iii) logical relations between said input states and said output states, whereby said output states depend on said input states according to said logical relations. The normalized influence matrix of the first embodiment defines said defined relative changes of each output class from a first input state to a second input state. The measured relative changes of the first embodiment are provided by data from one or more network testing experiments. The network testing experiments comprise measuring relative changes of one or more cellular constituents for a first input state to a second input state.

In a first aspect of the first embodiment, the step of determining how well each measured relative change matches each defined relative change comprises determining the values of an objective function of the differences between each of the measured relative changes and each of the defined relative changes.

In a second aspect of the first embodiment, the invention provides: first, that the step of determining further comprises determining a goodness of fit for each cellular constituent, wherein the goodness of fit is the maximum value of the objective function for the measured relative change of the cellular constituent; and second, that the overall goodness of fit is obtained by combining the goodness of fit values of each cellular constituent.

In a third aspect of the first embodiment, the invention further comprises a step of assessing the significance of the overall goodness of fit by a method comprising: (d) obtaining an expected probability distribution of overall goodness of fit values; and (e) assessing the statistical significance of the actual overall goodness of fit value in view of the expected probability distribution.

In a fourth aspect of the first embodiment, the invention further provides that step (d) of obtaining an expected probability distribution comprises: (i) randomizing the measured relative changes with respect to the cellular constituents; (ii) determining a "randomized" goodness of fit value for each cellular constituent by determining the maximum value of the objective function for the randomized measured relative change of the cellular constituent; (iii) determining an overall randomized goodness of fit value by combining said randomized goodness of fit values of each cellular constituent; and (iv) repeating steps (i) through (iii) to determine a plurality of overall randomized goodness of fit values, whereby the plurality of randomized goodness of fit values thus obtained comprises the expected probability distribution of overall goodness of fit values.

In a second embodiment, the present invention provides a computer system for testing a network model in a biological system comprising a processor and a memory coupled to the processor which encodes one or more programs, and wherein the programs cause the processor to perform a method comprising the steps of the above method.

In a particular aspect of the second embodiment, the programs further cause the processor to construct an influence matrix for a network model, wherein the constructed influence matrix is the normalized influence matrix used in the steps of the above method.

4. BRIEF DESCRIPTION OF THE DRAWINGS

These and other objects, features, and advantages of the invention will become apparent to those of skill in the art in view of the accompanying drawings, detailed description, and appended claims, where:

FIG. 1 illustrates generally the methods for testing a network hypothesis according to this invention;

FIGS. 2A–B illustrate a first exemplary network model according to this invention;

FIGS. 3A–C illustrate a second exemplary network model according to this invention;

FIGS. 4A–B illustrate a third exemplary network model according to this invention;

FIGS. 5A–B illustrate a fourth exemplary network model according to this invention;

FIG. 6 illustrates an exemplary feedback control network model according to this invention;

FIG. 7B illustrates an unnormalized influence matrix for the network model of FIG. 7A;

5. DETAILED DESCRIPTION

This section, first, generally describes the present invention, and second in subsequent subsections, presents details of individual steps and elements of this invention.

Figure 1:
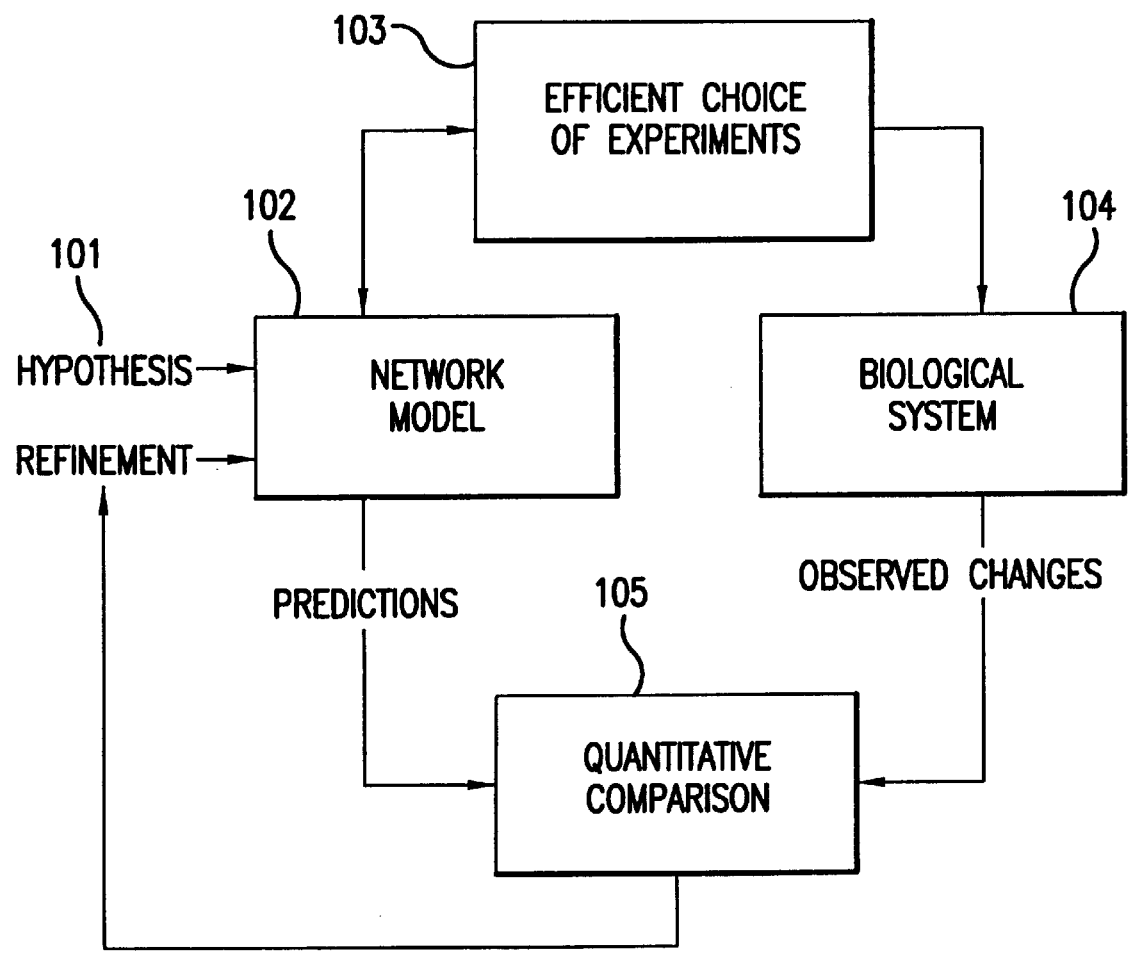

FIG. 1 illustrates generally the methods of this invention for testing hypotheses concerning network models present in a biological system. According to this invention, a network model includes a collection of related cellular constituents which are hypothesized to affect the biological system (e.g., a cell, an organism, a patient, and so forth) in particular manners. The mechanisms by which the effects occur may be known or suspected, and can accordingly guide selection of a network model, which can then be refined according to this invention. Alternatively, these mechanisms may not be known, in which case a network model, which is initially guessed, can be refined to fit experimental data according to this invention. The cellular constituents present in a network model and measured in a biological system can be of any type. For example, they can be, inter alia, abundances of mRNA species (representing gene expression), or abundances of protein species, or activities of protein species.

Therefore, with respect to FIG. 1, the methods of this invention begin with initial hypothesis 101 concerning the relationships and influences of the cellular constituents forming the biological network. This initial hypothesis, and subsequently refined hypotheses (if any), is precisely expressed in network model 102, which is represented, equivalently, as either one or more relations linking network inputs and outputs, or as a diagram representing these relations and also linking the inputs and outputs. The inputs represent perturbations or modification to the cellular constituents present in the network model, and the outputs represent classes of generic responses that any other cellular constituents not present in the network can assume upon perturbation or modification to the inputs. In other words, according to the network model, any cellular constituent in the biological system not present in the network should behave according to one of the generic output classes in response to perturbations or modifications of the pathway inputs.

Experimentally, network model 102 is tested and confirmed according to the other steps of the embodiment illustrated in FIG. 1. At step 103, the network model is processed, preferably automatically, to produce a set of efficient experiments that will be necessary and sufficient for testing or confirmation of the network. These experiments consist of input perturbations or modifications to the cellular constituents (which must be experimentally feasible), and are performed on biological system 104. Changes to other cellular constituents in the biological system (not perturbed as part of the network) are observed during these experiments. Similarly, network model 102 necessarily can be processed to predict the results of the efficient experiments when performed on the biological system 104.

Next, at step 105, a quantitative comparison is made of the experimentally observed changes to these predictions in order to determine how well the generic output classes of the network model fit the responses observed in the biological system. Preferably, this quantitative comparison includes also assessing the statistical significance of the fit. In view of this fit, the initial network model (or currently refined version) can be (further) refined and tested by repeating the previous steps.

In the following sections, details of these steps and their practice are described. Section 5.1 describes biological networks, network models, and a preferred notation for network models according to this invention. The preferred notation provides for clear and unambiguous description of network models. Section 5.2 describes quantitative measures suitable for expressing changes observed in cellular constituents during experiments on a biological system, predictions of changes in cellular constituents according to a network model, and assessment of the goodness of fit of a prediction to experimental results as suitably expressed. Section 5.3 describes determination of the statistical significance of a fit of experimental data to a network model, which is preferred as part of the quantitative comparison of the network model to the biological system. Section 5.4 describes how efficient experiments for testing and confirming a network model are chosen. Section 5.5 describes actual experimental techniques that can be used both to modify or perturb cellular constituents input to a biological network and also to measure the changes in general cellular constituents.

Finally, Section 5.6 describes an exemplary computer implementation of the methods of this invention.

5.1. NETWORK MODEL REPRESENTATION

This section describes, first, network models generally in the context of this invention, second, several examples of network models, and third, treatment of networks with feedback. This section concludes with a general description of the "cellular constituents" of interest in this invention.
Network Models Generally Biological network models in this invention simply relate a chosen set of cellular constituents (known as the "input" cellular constituents, or "input constituents") to other constituents in the biological system (such as, a cell or an organism). The chosen cellular constituents can be, for example, a set of proteins or genes of relevance for the action of a drug of interest. Network models relate modifications or perturbations to these input constituents, perhaps caused by exposure to a drug, to resulting responses in the other cellular constituents, i.e., to the corresponding "output state". Alternatively, network models also relate the absence of such perturbations to the input constituents, such as those found in a "resting state", to the corresponding output state. Since these models are directed to elucidating situations in which knowledge is limited or imperfect, they abstract away important details in order to promote effective modeling. In particular, network models in this invention preferably abstract both details of the biological mechanisms of action of the input cellular constituents and also the numerical details of the actual actions of the input cellular constituents.

Especially, the level of detail to which the network model reflects effects in the biological system is important in this invention. It is a fundamental discovery upon which this invention is based that, although in reality perturbations or modifications to input cellular constituents of a network and subsequent changes in other cellular constituents in the biological system are continuous, having a range of actual abundances or activities, important and useful information on biological systems can be obtained with only a coarse, discrete (often binary) abstraction and representation of these perturbations and changes.

Accordingly, in this invention, the values of modifications or perturbations to cellular constituents input to a network are represented by binary quantities, conventionally signified by the values "0" and "1". In other words, perturbations or modifications are considered for the purposes of this invention to be either present or absent. Typically, a reference state of an input constituent is denoted by "0". For example, "0" can be used to denote the normal occurrence of an mRNA species, the normal occurrence of a protein species, or a normal activity, or the absence of a drug or other non-normally occurring perturbation. On the other hand, by way of example, "1" can be used to denote the presence of a gene deletion preventing expression of a normally occurring mRNA, or a perturbation to a protein abundance or activity, or the exposure to a drug. However, "0" can also denote the occurrence of a first perturbation to a cellular constituent, while "1" denotes the occurrence of a further perturbation. The "state" of the inputs, or "input state", is taken to mean herein a collection of perturbations or modifications that can be applied to the input cellular constituents (also taking into account those cellular constituents that are unperturbed).

Additionally, in this invention, the output classes are taken to be boolean functions of the values of the perturbations or modifications to the input cellular constituents. Each output class has a unique pattern of binary values in response to a particular set of perturbations to the input cellular constituents of the biological network. The unique pattern of binary values associated with a particular output class is referred to herein as an "output state". As is well-known in the art, such boolean functions can be represented in standard formats by use of the elementary AND, OR, and NOT operators acting on variables representing values of the perturbations. Alternatively, these boolean functions can be represented as a network (also called herein a "graph") in which the nodes stand for the elementary boolean operators and in which the links stand for influences propagated from input cellular constituents, from the other nodes, or to output classes. Although actual biological mechanisms and pathways are not logical AND, OR, or NOT operators, the inventors have discovered that a model based on such logical constructs is rich enough to obtain useful conclusions about actual biological network connectivities and influences. As discussed subsequently, without loss of generality of application, the network models of this invention can be assumed to have no feedback loops.

To facilitate clear specification of network models, the boolean functions relating system inputs and outputs are unambiguously notated in formats known in the logical arts. Exemplary illustrations of this standard notation are presented in the subsequent examples.

The interpretation of the actual values, either "0" or "1", appearing at the output classes depends on a second fundamental discovery, which forms a further basis of this invention. According to this second discovery, testing and confirmation of network hypotheses is surprisingly simplified by considering only experimentally observed differences between two states of the inputs to a network model, such as differences between a reference state and a perturbed state or between two differently perturbed states. Since testing and confirmation of a network model does not depend on the (absolute) abundances or activities of cellular constituents in a single state, and since model-data comparisons will be based always on changes in the outputs, no particular meaning need be assigned to the actual binary values in the output class in all cases. For example, "0" may stand for the presence or absence or intermediate value of a particular cellular constituent, while "1" may conversely stand for absence or presence or a different intermediate value, respectively, of that cellular constituent.

Alternatively, an intermediate state (e.g., not completely "on" or "off" in the case of gene expression, or partial inhibition in the case of a drug treatment) of a given input to the network model can be interpreted as the "0" state, while any other state can be interpreted as the "1" state. Also, multiple intermediate states may be used to accomplish a change at the outputs, the presence or absence of this change then informing the connectivity of the network. Continuous control of specific gene and protein function can be used to accomplish these intermediate states, as described below in Subsection 5.5.1.

Because this invention employs experimental comparisons of changes between two states of the inputs to a biological network, what is experimentally significant are the relative values of the cellular constituents produced by the two states and what is significant in an output class are comparisons of the values generated by different states of the inputs. Such comparison can reveal changes (from "0" to "1" or from "1" to "0") or no changes (from "0" to "0" or from "1" to "1") between two states. In a preferred embodiment, these comparisons in an output class are subject to a further coarse grained abstraction which abstracts away further aspects of the predicted changes. In particular, aspects of the changes are abstracted from the occurrence of changes. The abstracted changes are collected in a matrix known herein as an "influence matrix", which represents the experimental predictions of a network model.

Several levels of abstraction, or "coarsenings", are used as is appropriate to the degree of knowledge present in the network model. In general, the more that is known about a particular biological network, the more detailed an abstraction can be usefully employed. For example, where little is known a priori concerning a particular biological network, the most coarse representations may be appropriate. In such a representation, values in the influence matrix can signify only that cellular constituents changed or did not change in a comparison between two input states (experiments), with even the direction of change ignored. Where more is known about the network, values in the influence matrix signify that cellular constituents increased or decreased, or vice versa, in a comparison between two input states. In an even less coarse representation, the influence matrix values can also represent the specific direction of change for each constituent in each comparison.

As an example of a high level of abstraction, a network of connections and gates can represent propagation of change rather than absolute state. For example, a differential pair of input states can be formed by changing any one input between two unsaturated values. The influence matrix element corresponding to a given output class response to that input is then set to "1" if there is any network path connecting the input to the output, and to "0" if there is not. The Boolean gates forming the connecting nodes of the network then are in effect all set to "OR" gates. The state of any input is "1" if it supplies a differential pair of input values, and the output of any gate is "1" if any of the inputs is "1". The interpretation of the logical gates then is as propagators of change, rather than absolute states. The model-data comparison procedure presented below can be applied intact since the comparison is done at the level of change vs. no change, not absolute state. Methods for these continuously variable perturbations include titratable expression systems, transfections, and drugs of specific known action, and are discussed in more detail in Section 5.5.1 below.

Importantly, as described, according to this invention network models can be iteratively refined by repetitive application of the steps of this method. Thus, even where a most coarse representation is used initially, refinement of the model can lead to additional experiments and additional knowledge of the network which permit use of refined models that are less coarse. Alternately, if the initial model does not well fit the experimental data, it can be first coarsened to simplify the search for improved models that may have significantly different structures.

A network model is used in this invention, at least, both to derive experiments for its testing and confirmation and also to predict the results of such experiments. Thus, from this network model, possible experiments are derived in a routine, preferably computer-implemented, fashion which are preferably both complete and also efficiently test and confirm the network model. See, infra, Section 5.4. The derived experiments are complete in the sense that any pair of output classes is distinguished by at least one experiment. The experiments are efficient in that they minimize some objective experimental design criteria, such as, for example, being least costly or most rapid to perform. Alternately, experiments can be simply chosen in other manners, such as by routine inspection, experimental intuition, or simply to include all possible comparisons (possibly then returning redundant information). These experiments are performed on a biological system, and the changed cellular constituents observed. In general, appropriate characteristics (e.g., abundance, activity, or so forth) of the changed cellular constituents are compared in the two states of the input cellular constituents defining each experiment in order to obtain relative values.

In addition to leading to an efficient choice of testing experiments, a network model also predicts the results of these experiments. See, infra, Section 5.2. Generally, according to a particular network model, the influence matrix collects the expected results of experiments (which compare pairwise the results of certain sets of perturbations to the input cellular constituents) according to the degree of abstraction or coarseness adopted in the particular model. Accordingly, a quantitative comparison of the network model checks how well all changes observed in the cellular constituents of the biological system can be classified or fit into one of the output classes of the biological network. The better this overall fit, the better is the network model. Preferably, the quantitative comparison returns a numerical value indicative of the goodness of the overall fit.

In a preferred embodiment, quantitative comparison 105 further includes statistical tests of the significance of the goodness of the overall fit found for the network model. See, infra., Section 5.3. These tests construct an empirical probability distribution against which to test the actual network model against a null hypothesis, which is that the network model has no relation to biological system 104. These tests yield a numerical probability value (also called herein a "P-value") that the network model has no relation to the biological systems.

Optionally, the initial network hypothesis can be iteratively refined by repetition of the previous steps in view of the P-values determined. For example, the initial network hypothesis can be altered or refined and the previous steps repeated to obtain a new P-value. If the new P-value is better than the initial P-value, the refined hypothesis can be used as the base for further refinements in a search for models with even better P-values. The goal of such refinement is convergence of the network models towards one with a P-value below some threshold of significance or towards one that is a useful representation of aspects of the biological system, or the biological subsystem, under study. Typical threshold P-values are no more than 36%, preferably no more than 5%, and even more preferably no more than 1% (chance that the network model has no relation to the biological system).

Examples of Network Models

Figure 2A:
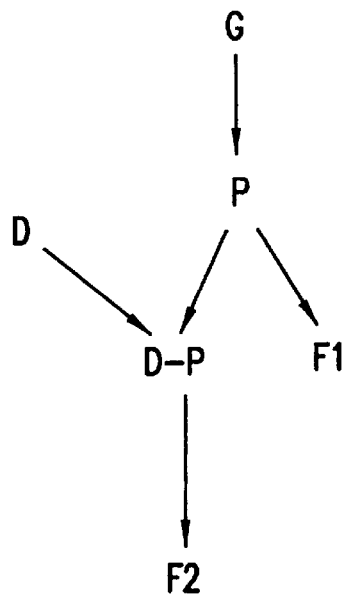
Figure 2B:
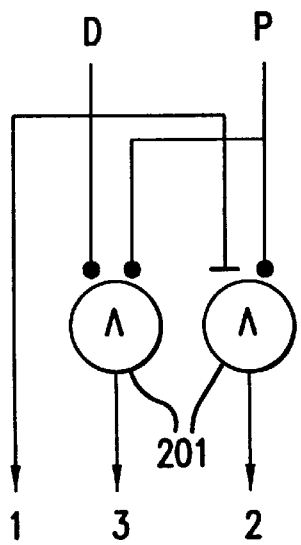

Several examples of network models presented in a preferred notation are presented in the following. A first network model is illustrated in FIG. 2B, with the underlying biological activity illustrated in FIG. 2A. According to FIG. 2A, protein P is expressed by gene G, and is normally directed to functions F1. Upon combination with drug D, however, protein P is re-directed to new set of functions F2. Since the combination of drug D with protein P removes some of the molecules of protein P from their original function, F1, there is one class of effects associated with loss of the original function of protein P. Since the complex of drug D with protein P produces new function F2, there is another class of effects associated with this complex. This type of drug action, which can be called "protein re-direction", is exemplified by the action of immunosuppressants Tacrolimus (FK506) and Cyclosporin A on the calcineurin protein via their respective binding partners, FK506 binding protein and cyclophilin (Cardenas et al, Perspectives in Drug Discovery and Design, 2:103–126, 1994). For example in FIG. 7B, output classes 1, 2, and 3 represent redirection of protein fpr by the drug tacrolimus, and output classes 5, 6, and 7 represent redirection of protein cph by the drug cyclosporin A.

FIG. 2B illustrates a network model which is a precise representation of these effects in terms of logical operations and connections. Inputs are labeled by D, for exposure to drug D, and P, for perturbation of protein P (such as by deletion of gene G). Nodes 201 represent logical operations which are labeled by their operator, in this case "A" for the AND operator. The meaning of the links between the nodes are indicated by the legend appearing in this figure. The output classes 1, 2, and 3 label arcs exiting from the network. (This format of diagrammatic notation is employed throughout this description.) This diagram is equivalent to following the Boolean relations for the output classes:

Output class 1=D

Output class 2=P A ⁻D

Output class 3=P A D where "A" denotes logical AND, and "⁻" denote logical NOT.

The output classes are also represented by Table 1 (also known as a "truth table" in the arts).

TABLE 1

OUTPUT CLASSES OF FIG. 2B

| Output Class | D = 0, P = 0 state 1 | D = 1, P = 0 state 2 | D = 0, P = 1 state 3 | D = 1, P = 1 state 4 |
|---|---|---|---|---|
| 1 | 0 | 1 | 0 | 1 |
| 2 | 0 | 0 | 1 | 0 |
| 3 | 0 | 0 | 0 | 1 |

In this table, the top row lists sets of possible values for the input perturbations or modifications to the network model of FIG. 2B. As described, each set is called an input state and each state is labeled in the second row of this table. The network model describes three output classes that are hypothesized to explain all the effects of this network on the containing biological system. Output classes 1, 2, and 3 have the values in the various input states listed in the following rows of Table 1.

Output classes 1, 2, and 3 of FIG. 2B model behavior of cellular constituents when the biological system (or cell) is subject to the listed input states. As further described subsequently, the cellular constituents can be, inter alia, mRNA abundances (representing gene expression), protein abundances, or protein activities. Use of this network model according to this invention does not require apriori knowledge concerning which particular cellular constituents are modeled by which particular output classes. Rather, the goodness of this network model is determined by how well observed changes in cellular constituents are modeled by one of these classes in response to experiments on the system.

According to this invention generally, the output classes are preferably disjoint sets. In other words, if there is an effect of drug D on a cellular constituent which is not mediated by P (output class 1) then this cellular constituent is not also affected by drug D via protein P, nor is it affected by protein P directly (output classes 3 and 2). Use of disjoint output classes has been found to be effective in that it generally models observed biological systems and simplifies subsequent analysis of the network model.

Also as described, values of the output classes in various states are not given an absolute interpretation. Instead, they are compared for relative changes. Accordingly, experiments for testing this network model compare changes in cellular constituents between pairs of states of the input cellular constituents, drug D and protein P. This comparison is possibly abstracted, as described above and in more detail in Section 5.2. For example, Table 2 present the results of experiments 1, 2, and 3 on the network model of FIG. 2B.

TABLE 2

EXPERIMENTS TESTING FIG. 2B

| Output Class | +/− Drug (+ Protein) Experiment 1 (state 4 vs. state 3) | +/− Protein (− Drug) Experiment 2 (state 3 vs. state 1) | +/− Drug (− Protein) Experiment 3 (state 2 vs. state 1) |
|---|---|---|---|
| 1 | 1/0 | 0/0 | 1/0 |
| 2 | 0/1 | 1/0 | 0/0 |
| 3 | 1/0 | 0/0 | 0/0 |

In Table 2, the three columns present the results of the three different experiments: experiment 1 compares the response of a biological system with and without drug D exposure with protein P present; experiment 2 compares the response of the biological system with and without the protein P present in the absence of exposure to drug D; and experiment 3 compares the response of the biological system with and without exposure to drug D and with protein P absent. The entries of Table 2 are directly obtained from the corresponding entries of Table 1.

The systematic choice of experiments for testing a given network model is described in Section 5.4. Protein P may be perturbed to be absent by, for example, deletion or knockout of gene G (of FIG. 2A) by techniques known in the art and set out in Section 5.5.

For any cellular constituent, although the meaning of the absolute values "0" or "1" is arbitrary, changes are significant. In a lowest level of abstraction, a change from "0" to "1" is taken to be in a direction different from a change from "1" to "0". In a preferred level of abstraction, a change from "0" to "1" is taken to be merely different from a change from "1" to "0". In a highest level of abstraction, a change from "0" to "1" or a change from "1" to "0" is taken to be different from no change. These abstractions are used to predict the results of experiments as described in Section 5.2.

For the example experiments of Table 2, the behavior of each class in the three experiments is distinct. Thus cellular constituents (for example, gene or protein abundances or activities) with clearly observed responses may be fit by one of the three classes, based on their responses to these three experiments, or may not be so fit. Some cellular constituents may have observed behaviors that do not fit any of the classes due simply to experimental errors or inaccuracies in the network model assumptions of FIG. 2B. Other cellular constituents may have only small observed changes that are not statistically significant and cannot be placed with confidence into any class. In all cases, according to this invention it is the over-all quality of fit into the output classes of the observed behaviors of all the cellular constituents that is a measure of the quality of the network model. Preferably, the method of fitting returns a numerical value representative of the quality of the fit.

Alternative models are advantageously compared by comparing the quality of fit. For example, a network model alternative to that of FIG. 2B can omit the effects of the complex of drug D and protein P on the biological system. Accordingly, output class 3 is not present and Table 2 then will lack the last row. There would then be only two output classes, and the observed behaviors of the cellular constituents would be modeled by class 1 or of Class 2. The quality of fit of this alternative model can be compared to the original model to determine the superior model.

The following are three additional examples of biological networks appropriate to simple biological situations. FIGS. 3A–C illustrate a model appropriate for a kinase cascade in a signaling pathway such as occurs in the mating pathway in yeast (Cardenas, et al., 1994, *Perspectives in Drug Discovery and Design* 2:103–126). FIG. 3A represents a biological mechanism in which signaling molecule S activates protein P1, which in turn activates protein P2, the latter in turn activating protein P3. Output classes 1 and 2 contain cellular constituents (for example, mRNA or protein abundances, or protein activities) whose abundances or activities are changed as a consequence of events upstream in this signaling pathway. Output class 3 contains the cellular constituents ultimately targeted by this signaling pathway.

FIG. 3B is a network model corresponding to the biological mechanism of FIG. 3A. FIG. 3C sets out the logical relationships modeled. Interactions at the proteins in this pathway are assumed to be modeled by AND operators, which means that both inputs (activation of the prior protein in the pathway and presence of the instant protein) must be present for activation. The primary biological function of this network is to effect ultimate changes represented by class 3, but side-effects can occur due to activities of the intermediate proteins P1 and P2. These side-effects are modeled by classes 1 and 2. Having all three classes allows reconstruction of the order of activation in this pathway, that is signal S activates protein P1, which activates protein P2, which activates protein P3, from observation of the changes in these other classes.

One of skill in the art will readily understand that the network model of FIG. 3B is equivalent to the logical relations of FIG. 3C. Further, one of skill in the art will also readily understand how to translate either of these representations in a state truth table, similar to Table 1, and an experimental results table, similar to Table 2.

FIGS. 4A–B are appropriate to a biological situation in which a transcription complex is formed of proteins P1, P2, and P3 that regulates expression of gene G4, from which protein P4 is expressed. The three transcription factors operate on gene G4 in a multiplicative manner, in which the expression of gene G4 depends on the product of the bound amounts of all three factors. FIG. 4A represents this biological mechanism. FIG. 4B is a corresponding network model in which the multiplicative action of the transcription factors is represented by an AND operator. Also illustrated is the logical relationship describing the single output class. Although, like the multiplicative action, the AND operator requires all the factors to be present for the activation of gene G4, this operator is insensitive to the amounts of the bound factors. Thus, the network model, consistent with the binary approximation on which this invention is based, abstracts from the actual values of the transcription factors only that each factor is present or absent.

FIGS. 5A–B are appropriate to a situation involving redundant transcription factors. Here, if either protein P1 or protein P2 is present in sufficient amount, transcription of G3 is induced in an amount corresponding to that amount. FIG. 5A illustrates this biological mechanism, and FIG. 5B illustrates the corresponding network model. Also illustrated is the logical relationship describing the single output class. Although, like the alternative action of the redundant transcription factors, the OR operator requires only the presence of one of the factors for the activation of gene G3, this operator is insensitive to the amount of the factor present. Here, also, this network model abstracts a binary approximation of the underlying biological system.

In view of these examples, one of skill in the art will understand how to construct network models from hypothetical biological mechanisms that are suitable for the practice of the subsequent steps of this invention. Alternatively, one of skill can construct network models from consideration of the patterns present in actual experimental data without prior knowledge of any biological mechanisms.

Treatment of Networks with Feedback

Network models of this invention do not include feedback between the logical operations in a network, because such feedback prevents unambiguous determination of responses of the output classes in terms of states of the cellular constituents input to the model. Although feedback is known and expected to be a ubiquitous feature of many biological mechanisms and systems, its absence from the network models of this invention is not limiting for at least the following reasoning.

Generally, feedback in biological systems is known to tend to mute the effects of perturbations without eliminating the effects or reversing the direction of the effects of perturbations. Since the present invention is based on binary abstractions of changes in the values of characteristics of cellular constituents, feedback will not change measured inputs to network models nor measured changes used for model testing and confirmation. In other words, as long as perturbations cause observable changes in the same directions to cellular constituents with and without feedback, feedback need not be considered in the network models used in this invention since these models are insensitive to actual numerical values.

These properties and effects of perturbations are illustrated by the example illustrated in FIG. 6. FIG. 6 illustrates the simplest stable feedback network. Here, cellular constituent B inhibits cellular constituent A (by the curved inhibitory link), while cellular constituent A activates cellular constituent B (by the straight excitatory link). This network includes cases where A and B can be any type of cellular constituent, for example, inter alia, mRNA abundances, protein abundances, protein activities. A and B can also represent entire biological subsystems, perhaps in turn represented by their own network models.

In the following simple feedback model, which is often a useful approximation for biological systems, the characteristics of A and B, e.g., their abundances or activities, which are denoted by [A] and [B], respectively, are governed in time by the following differential equations.

$$\frac{d[A]}{dt} = a + \beta_1[B] - \alpha_0[A] \tag{1}$$

$$\frac{d[B]}{dt} = b - \alpha_1[A] - \beta_0[B]$$

In these equations: "a" and "b" are positive rates of creation of A and B, respectively; $\alpha_1$ is the positive constant of inhibition of B by A; $\beta_1$ is the positive constant of activation of A by B; $\alpha_0$ and $\beta_0$ are positive rates of degradation of A and B, respectively.

First, it can be readily determined that these equations have a stable equilibrium for A and B if the following relation holds: $\alpha_0 b > \beta_0 a$. In this stable equilibrium, the values of [A] and [B] are less than they would be if the feedback inhibition were absent from these equations (that is, if $\beta_1$ were 0). The feedback thus mutes the reference levels in this biological system. Second, intervening to perturb the network by forcing [A] to be 0 (or equivalently forcing [B] to be 0) produces a new equilibrium value of [B] (or [A]). The new value of [B] differs from the old value of [B] in the same sense whether or not feedback is present (that is, whether or not $\beta_1$ is 0). However, because values in the reference state are muted in the case of feedback, the numerical value of changes due to perturbation are also muted with feedback (as would be intuitively expected).

Accordingly, in this feedback network, as expected, the behavior, abstracted to consider only directions of change and not magnitudes of change, is the same as the behavior of the network without feedback. One of skill in the art will readily understand that, in view of the abstractions that are the basis of this invention, the absence of feedback in the network models of this invention does not limit the applicability of the methods of this invention to various biological systems.

Cellular Constituents of Interest

The network models of the invention include a limited set of input cellular constituents whose perturbation has effects on other cellular constituents of a cell, an organism, or a biological system generally. For convenience of description only and without any limitation, cellular constituents are conveniently classified as belonging to various aspects of the biological state of a cell. In this application, cellular constituents also conveniently are taken to refer to the presence of exogenous agents, whether naturally occurring in the cell or non-naturally occurring, such as drugs.

An aspect of the biological state of a cell, as used herein, is taken to mean the state of a collection of cellular constituents, which are sufficient to characterize the cell for an intended purpose, such as for testing and confirming a particular network model. Aspects of the biological state of a cell can include the presence or absence of exogenous agents, such as drugs, that are relevant to a particular network model. The modifications and/or perturbations and the measurements and/or observations made on the state of these constituents can be of their abundances (i.e., amounts or concentrations in a cell, the level of exposure to a drug), or their activities, or their states of modification (e.g., phosphorylation), or other measurement relevant to the testing and confirmation of a network model of interest. In various embodiments, this invention includes making such modifications and/or perturbations and such measurements and/or observations on different collections, or aspects, of cellular constituents. (As used herein, the term "cellular constituents" is not intended to refer to known subcellular organelles, such as mitochondria, lysozomes, etc.) In the following the various aspects of the biological state of a cell of interest in this invention are described. One aspect of the biological state of a cell usefully measured in the present invention is its transcriptional state. The transcriptional state of a cell includes the identities and abundances of the constituent RNA species, especially mRNAs, in the cell under a given set of conditions. Preferably, a substantial fraction of all constituent RNA species in the cell are measured, but at least, a sufficient fraction is measured for testing and confirming a particular network model of interest. The transcriptional state is the currently preferred aspect of the biological state measured in this invention. It can be conveniently determined by, e.g., measuring cDNA abundances by any of several existing gene expression technologies.

Another aspect of the biological state of a cell usefully measured in the present invention is its translational state. The translational state of a cell includes the identities and abundances of the constituent protein species in the cell under a given set of conditions. Preferably, a substantial fraction of all constituent protein species in the cell are measured, but at least, a sufficient fraction is measured for testing and confirming a particular network model of interest. As is known to those of skill in the art, the transcriptional state is often representative of the translational state.

Other aspects of the biological state of a cell are also of use in this invention. For example, the activity state of a cell, as that term is used herein, includes the activities of the constituent protein species (and also optionally catalytically active nucleic acid species) in the cell under a given set of conditions. As is known to those of skill in the art, the translational state is often representative of the activity state.

This invention is also adaptable, where relevant, to "mixed" aspects of the biological state of a cell in which measurements of different aspects of the biological state of a cell are combined. For example, in one mixed aspect, the abundances of certain RNA species and of certain protein species, are combined with measurements of the activities of certain other protein species. Further, it will be appreciated from the following that this invention is also adaptable to other aspects of the biological state of the cell that are measurable.

Perturbations or modifications to input cellular constituents to a biological network model will typically affect many other cellular constituents of whatever aspect of the biological state of a cell is being measured and/or observed in a particular embodiment of this invention (in addition to those cellular constituents that are directly modified). For example, as a result of the network model of interest as well as a result of other regulatory, homeostatic, and compensatory networks and systems known to be present in cells, perturbations to the inputs of a network model will have complicated and often unpredictable indirect effects throughout the cell or biological system. As a result of internal compensations, many perturbations to a biological system, although having only a muted effect on the external behavior of the system, can nevertheless profoundly influence the internal response of individual elements, e.g., gene expression, in the cell.

Perturbing the inputs to a network model of interest is considered here as an example of the above principles. Although these perturbations will directly affect only the outputs of that biological network, additional cellular constituents that are inhibited or stimulated by these outputs, or which are elevated or diminished to compensate changes in these output will also be affected. Still other cellular constituents will be affected by changes in the levels or activity of the second tier constituents, and so on. Therefore, the direct effects of the biological network are hidden in a potentially large number of indirect effects downstream from the network.

According to the present invention, the analysis of all these downstream effects provides considerable information useful for testing and confirming the particular network model. If the network model is useful, the relative changes observed for the responding cellular constituents should be fit by one of the output classes of the model. Where the exact nature and mechanism of these downstream effects are not clearly known, use of one of the abstractions for predictions of experimental results according to this invention can be advantageous. For example, the direction of changes can be ignored, and the model can fit patterns of change or no-change produced by various states of perturbations of the cellular constituents input to the model. Alternately, in a lower level of abstraction, the model can fit patterns of change in one direction, change in the other direction, and no-change (ignoring the sign of the direction of change). This invention is adaptable to other levels of abstraction.

5.2. EXPERIMENTAL TESTING OF A NETWORK MODEL

This section describes how a network model is tested and confirmed by comparison to experimentation data. Preferably, first, direct experimental observations of cellular constituents in the two states of each experiment are converted into useful measures of the relative changes of these constituents between the two states. Second, an influence matrix containing the abstracted predictions of the network model is constructed directly from the model. Finally, third, the observed measures of relative change for each cellular constituent are assigned to the best output class according to the influence matrix and an overall goodness of fit is found for the network model.

Section 5.3 then describes determining a statistical measure of the significance of the overall goodness of fit. Methods for choosing experiments for testing and confirmation of a network model are described in Section 5.4.
Measures of Relative Change of Cellular Constituents Experiments used for testing and confirming a network model according to this invention comprise differential expression measurements wherein characteristics of cellular constituents are measured or observed in two different states characterized by different perturbations or modifications to the cellular constituents that are input to the model. For example, expression of genes in a cell can be observed by measuring cDNA levels derived from cellular RNA in one state in which the cell is not exposed to a drug which inhibits a protein input to a network model of interest and another state in which the cell is exposed to that drug.

In general, experimental data consists of, inter alia, measurements or estimates of abundances of individual mRNA species, or of individual protein species, or of activities of individual proteins, and so forth. For each cellular constituent there are two measurements for each experiment obtained from the two states of perturbation of the input cellular constituents.

Differential expression measurements will suffer from many biases despite efforts to design the experiment so that most errors cancel in the difference, or ratio, between the two measurements. Individual molecular species will amplify, label, and hybridize in ways that depend differently on the two fluorescent labels, so that each gene will have its own peculiar bias. These biases can be reduced by averaging pairs of experiments in which the fluor assignment is reversed between the two members of the differential pair. Biases also may be removed by detrending the ratios vs. the controlling parameter, such as open reading frame (ORF) length (longer genes are reverse-transcribed less efficiently with one fluor vs. another), when such a controlling parameter can be identified.

As described, the methods of this invention compare predictions of a network model to the relative values of cellular constituents determined from observations in these two states. Using relative values is advantageous in that systematic errors in the experimental measurements can substantially cancel from such relative values and in that the effects of uncertainties or lack of knowledge in the network model are significantly reduced. Detail in the experimental results not predictable by the network model is abstracted away.

These relative values can be determined in different manners from the corresponding experimental values. In one embodiment, relative values can be simply ratios between the values observed in the two input states. It is not preferred to use differences of the corresponding values, since multiplicative effects have been found to have greater significance than additive effects across a wide range of observed values. In place of ratios, which become 1 in the case of no change, it is more preferable to use a logarithm (to some base) of the ratios of observed values, which become 0 in the case of no change. Other monotonic functions similar to logarithms can be used in place of logarithms. For example, a change from 1 to 4 copies per cell of a first mRNA species is likely to have similar significance to a change from 200 to 800 copies per cell in a second mRNA species. On the other hand, a change from 200 to 203 copies per cell in that second mRNA species is likely to have far less significance.

Additionally, the relative values determined also preferably give greater weight to the same multiplicative change if the associated cellular characteristic is, e.g., more abundant active, or so forth. This is because that larger fractional measurement errors are likely to be present in data for cellular constituents that are less abundant, active, or so forth. For example, a measured change from 1 to 4 copies per cell of a first mRNA species is likely to be not as statistically significant as a measured change from 200 to 800 copies per cell in a second mRNA species.

A preferred measure of relative values, therefore, behaves similarly to a logarithm of the ratios of observed values for measurements of species that are abundant or active, or so forth, while it tends toward zero for measurements of species whose abundances, activities, and so forth are sufficiently small that their measurements are likely to be dominated by statistical errors. An example of such a preferred function for determining relative change from observed values is given by the following equation.

$$x = \frac{([A])_2 - ([A])_1}{(\sigma^2 + f^2(([A])_2 + ([A])_1)^2/4)^{1/2}} \quad (2)$$

In this equation: $[A]_1$ and $[A]_2$ are the values measured for cellular constituent A in the two states being compared; "$\sigma$" represents an expected additive RMS measurement error; and "f" represent an expected multiplicative fractional error level. The denominator of this equation is the combined additive plus multiplicative RMS measurement error. The additive RMS error level, "$\sigma$", and the multiplicative RMS error level, "f", are determined as is well-known in the art.

This determination of relative values is advantageous for the following reasons. First, this equation behaves like the logarithm of $[A]_2/[A]_1$ for small fractional changes of $[A]$ at high values of $[A]$, and approaches zero for values of $[A]$ small compared to the additive error level, $\sigma$. This equation also approaches to $\pm f^{-1}$ for A>>B, $\sigma$ (">>" denotes much greater) or B>>A, $\sigma$. This latter property prevents undue weight being attached to any large single change, either increase or decrease, measured for one cellular constituent while retaining quantitative information about the degree of change for all the cellular constituents, in that larger ratios of $[A]_2$ to $[A]_1$ result in larger values for x. Finally, for modest ratios of $[A]_2$ to $[A]_1$, this equation measures relative changes in units of the standard deviations, "$\sigma$", assumed for measurement errors.

In a preferred embodiment where the transcript state of a cell is measured by transcript arrays (see Section 5.5), Equation 2 has particularly preferred properties. The additive RMS error levels arise from, e.g., background fluctuations in hybridization to oligomers on the transcript array, image acquisition of fluorescent spots, image processing, and so forth. The multiplicative RMS error levels arise from, e.g., systematic variations due to overall system gain fluctuations, variations in processing due to different properties of the two phosphors, and so forth.

This invention is equally adaptable to other determinations of relative values that have similar advantageous properties. For example, although not as well behaved for small values of $[A]_1$ and $[A]_2$, an alternative measure of relative values is the logarithm of the ratio $[A]_2/[A]_1$.

Construction of an Influence Matrix

The experimental predictions derived from a particular network model are contained in an array called herein the "influence matrix". The influence matrix is denoted by "g" and has elements denoted by "$g_{ni}$". In detail, "$g_{ni}$" signifies the behavior predicted in the $n^{th}$ output class in response to the $i^{th}$ experiment. The value of the elements of g depend on the level of abstraction, or "coarseness" of the model, that is whether or not the model is sufficiently detailed to predict the relationship between the sign of the changes in the different output classes in response to the experiments.

The influence matrix is constructed from a network model and a set of experimental comparisons according to a two step process: first, an unnormalized influence matrix is constructed; and second, the unnormalized matrix is normalized. Concerning the first step, each experiment of the set of experimental comparisons specifies a comparison between two states of the biological system, each of the states being defined by a certain pattern of perturbations or modifications, or by the absence of perturbations of modifications, to the cellular constituents input to the network model. Using any convenient one of the equivalent representations of the network model, which are, inter alia, as a network diagram, as logical relations, or as a truth table, the predicted responses of each of the classes to each experiment is mechanically determined. These responses are either changes (from "0" to "1" or from "1" to "0") or no changes (from "0" to "0" or from "1" to "1") between two experimental states.

An unnormalized influence matrix is constructed from these predictions according to the level of abstraction, or coarseness, adopted for the model. In a preferred embodiment, there are two levels of abstraction, which are summarized in Table 3. According to the highest level of abstraction, only the fact that cellular constituents changed or did not change in a particular experimental comparison is considered. The direction of change is ignored. For this level, elements of the unnormalized influence matrix are selected from the third column of Table 3.

According to the next level of abstraction, the direction of change of cellular constituents is considered. This resulting influence matrix can be subsequently utilized to determine an overall goodness of fit in a first manner in which only the relative signs of changes in cellular constituents are considered. Here, it is assumed that the network model can only predict that a cellular constituent changed in opposite directions in two different experiments, but cannot predict in which direction it changed. In a second manner of processing, the network model is assumed capable of predicting the direction of change, and the direction of change is considered in determining an overall goodness of fit. For this level, elements of the unnormalized influence matrix are selected from the second column of Table 3.

TABLE 3

INFLUENCE MATRIX VALUES

| Value of $g_{ni}$ | The direction of change is considered | The direction of change is not considered (only change or no-change is considered) |
|---|---|---|
| −1 | decrease) (or increase) | no change |
| 0 | no change | model does not specify change |
| 1 | increase (or decrease) | change (increase or decrease) |

The unnormalized influence matrix is easily constructed to have one row for each output class and one column for each experimental comparison. The value of the element for the $n^{th}$ output class in response to the $i^{th}$ experiment, $g_{ni}$, is selected from the column corresponding to the appropriate level of abstraction and from the row corresponding to the predictions made for the $n^{th}$ output class in response to the $i^{th}$ experiment.

For example, Table 4 is the unnormalized influence matrix for the network of FIG. 2B in response to experiments 1, 2, and 3 set out in Table 2 of Section 5.1 for a level of abstraction in which the direction of change of cellular constituents is considered.

TABLE 4

INFLUENCE MATRIX FOR FIG. 2B

| | +/− Drug (+ Protein) Experiment 1 (state 4 vs. state 3) col. 1 (i = 1) | +/− Protein (− Drug) Experiment 2 (state 3 vs state 1) col. 2 (i = 2) | +/− Drug (− Protein) Experiment 3 (state 2 vs. state 1) col. 3 (i = 3) |
|---|---|---|---|
| Row of influence matrix | | | |
| $g_{1i}$ | −1 (change from 1 to 0) | 0 (no change) | −1 (change from 1 to 0) |
| $q_{2i}$ | 1 (change from 0 to 1) | −1 (change from 1 to 0) | 0 (no change) |
| $q_{3i}$ | −1 (change from 1 to 0) | 0 (no change) | 0 (no change) |

In contrast Table 5 is the unnormalized influence matrix for the network of FIG. 2B in response to experiments 1, 2, and 3 set out in Table 2 of Section 5.1 for a level of abstraction in which only that a cellular constituent changed or did not change is considered.

TABLE 5

INFLUENCE MATRIX FOR FIG. 2B

| | +/− Drug (+ Protein) Experiment 1 (state 4 vs. state 3) col. 1 (i = 1) | +/− Protein (− Drug) Experiment 2 (state 3 vs. state 1) col. 2 (i = 2) | +/− Drug (− Protein) Experiment 3 (state 2 vs. state 1) col. 3 (i = 3) |
|---|---|---|---|
| Row of influence matrix | | | |
| $g_{1i}$ | 1 (change) | −1 (no change) | 1 (change) |
| $g_{2i}$ | 1 (change) | 1 (change) | −1 (no change) |
| $g_{3i}$ | 1 (change) | −1 (no change) | −1 (no change) |

Next, the unnormalized influence matrix is normalized. Correct normalization insures that the somewhat arbitrary assignment of −1's, 0's, and 1's in Table 3 to various predicted changes does not skew the results of the goodness of fit determination. In the preferred normalization, each row of g is linearly normalized, independently of the other rows, in order to have a mean equal to zero and to have a sum of squares of the elements in each row (the standard deviation squared) equal to that of all the other rows.

Preferably, the standard deviation of all the rows is set to 1.

For example, according to this preferred normalization Table 4 results in the normalized influence matrix of Table 6.

TABLE 6

NORMALIZED INFLUENCE MATRIX FOR FIG. 2B

| Row of influence matrix | +/− Drug (+ Protein) | +/− Protein (− Drug) | +/− Drug (− Protein) |
|---|---|---|---|
| $g_{1i}$ | 0.58 | −1.15 | 0.58 |
| $g_{2i}$ | 1.0 | −1.0 | 0.0 |
| $g_{3i}$ | 1.15 | −0.58 | −0.58 |

Also, Table 5 results in the normalized influence matrix of Table 7.

TABLE 7

NORMALIZED INFLUENCE MATRIX FOR FIG. 2B

| Row of influence matrix | +/− Drug (+ Protein) | +/− Protein (− Drug) | +/− Drug (− Protein) |
|---|---|---|---|
| $g_{1i}$ | 0.58 | −1.15 | 0.58 |
| $g_{2i}$ | 0.58 | 0.58 | −1.15 |
| $g_{3i}$ | 1.15 | −0.58 | −0.58 |

Determining the Overall Goodness of Fit

Next, an overall goodness of fit of the network model to the set of experiments is determined, in view of the normalized influence matrix, by, first, assigning cellular constituents with observed changes to that output class which best matches the behavior of that cellular constituent in response to the various experiments of the set of experiments, and, second, by determining an overall goodness of fit in view of the goodness of fit of the individual cellular constituents. In a preferred embodiment, an objective measure provides a numerical indication for each changed cellular constituent of how well it fits each output class in the influence matrix. The cellular constituent is then assigned to the output class with the largest objective numerical indication, and that largest numerical indication is taken to be the goodness of fit of that cellular constituent. The overall goodness of fit of the network model is taken as depending monotonically on all the goodness of fit for the individual cellular constituents. For example, the overall goodness of fit is the sum of the individual goodness of fit.

A preferred objective measure is the correlation (also called in this case the "dot product") of the measure of changes observed for a cellular constituent according to the previous subsection with the rows of the influence matrix. For purposes of description only, it is convenient to assemble the changes observed for a cellular constituent in each experiment into a vector, x, each element of which is one of the measures of observed changes. Then, as is well-known in the art, a correlation of the ith row of the influence matrix with the observed changes is a sum of the products of corresponding elements of the row, $g_i$, and the vector, x, of changes. Correlation of all the rows of the influence matrix, g, with the observer changes is then simply the matrix product, g*x, of the influence matrix with the vector of changes.

In detail, in the case where only the fact of change or no-change in a cellular constituent is considered in constructing the influence matrix and the direction of change of the cellular constituents is ignored, then the correlation of the influence matrix is preferably with the absolute value of the changes. If |x| represents a vector whose elements are the absolute values of the elements of x, then in this case the correlation is g*|x| is the objective goodness of fit measure. The cellular constituent is then assigned to the output class whose row has the highest value in this correlation.

In the case where the relative direction of change of the cellular constituents is considered in constructing the influence matrix, and where the network model predicts only the relative direction of change, then the cellular constituent is assigned to the output class whose row has the highest absolute value in this correlation. In other words, in this case |g*x| is the objective goodness of fit measure.

Finally, in the case where the absolute direction of change of the cellular constituents is predicted in the network model influence matrix, then the cellular constituent is assigned to the output class whose row has the highest value in this correlation. In other words, in this case the simple correlation, g*x, is the objective goodness of fit measure.

In the following, "n(k)" is used to represent the output class that best fits observed and measured cellular constituent k according to the cases above.

For example, consider the normalized influence matrices of Tables 5 and 6, predicting the results of the network model of FIG. 2B in these first two cases above and a cellular constituent whose observed measure of change in experiments 1, 2, and 3 is observed to be the vector x=(+2.3, +1.2, −4.7). Correlation of x with Table 5 results in:

$$|g_1*x|=|(0.58,-1.15,0.58)*(2.3,1.2,-4.7)|=|-2.7|=2.7$$

$$|g_2*x|=|(1.22,-1.22,0)*(2.3,1.2,-4.7)|=|1.3|=1.3$$

$$|g_3*x|=|(1.15,-0.58,-0.58)*(2.3,1.2,-4.7)|=|4.7|=4.7$$

The cellular constituent with these observed changes is accordingly best fit by output class 3 (with the largest correlation value of 4.7), where the relative direction of change is predicted by the network model. Next, correlation of |x| (=(+2.3, +1.2, +4.7)) with Table 6 results in:

$$g_1*|x|=(0.58,-1.15,0.58)*(2.3,1.2,4.7)=2.7$$

$$g_2*|x|=(0.58,0.58,-1.15)*(2.3,1.2,4.7)=-3.4$$

$$g_3*|x|=(1.15,-0.58,-0.58)*(2.3,1.2,4.7)=0.75$$

In the case where the network model does not predict even the direction of change, this cellular constituent is best fit by output class 1 (with the largest correlation value of 2.7).

Once all cellular constituents with observed changes have been assigned to their best fitting output classes, an overall goodness of fit of the network model is determined as the sum of the individual correlation values of the best fitting output classes for all the observed cellular constituents. This overall goodness of fit can be represented by the following equations.

$$F = \sum_k |g_{n(k)} * x_k| \qquad (3)$$

$$F = \sum_k g_{n(k)} * |x_k|$$

In this equation, "F" represents the overall goodness of fit value and the other quantities have their previous meanings ("$x_k$" representing the measured changes for the k'th cellular constituent). The sum is over all observed and measured cellular constituents. The first equation is appropriate for the case where the relative direction of change is considered, and the second for the case where only change or no-change is considered. Alternatively, the overall goodness of fit can be any monotonic function of all of these correlation values.

In alternative embodiments, the cellular constituents with small or unobservable responses to the experiments perturbations can be excluded from the goodness-of-fit determination in order to reduce experimental noise. Objectively, a threshold can be set for the sum of the elements of $|x|$. On the other hand, including cellular constituents with small changes in the goodness-of-fit determination can capture the "ripple-down" effects of any perturbation of distantly related cellular constituents. Although individually not significantly measurable, these small effects can in the aggregate provide useful and significant information for testing or confirming the network model. The threshold for excluding cellular constituents with small changes can be set on a case by case basis.

Criteria for assigning a statistical significance to the overall goodness of fit is described in Section 5.3.

This invention is also adaptable to alternative embodiments of the goodness-of-fit determination. For example, in place of the absolute value function, the square function (or other monotonic positive function) can be used. A cellular constituent can be assigned to the output class with the greatest $(g*x)^2$ or $(g*x^2)$ (where $x^2$ denotes a vector whose elements are the squares of elements of x). Alternatively, the objective measure can be $(g*x^2)$ These alternatives generally do not change the output class assignments of cellular constituents, since they do not change the ranking of the magnitudes of the objective function. However, more weight is put on larger values of the measures of change of a cellular constituent when the fit values for all genes are combined to form an over-all fit value.

5.3. DETERMINING STATISTICAL SIGNIFICANCE

Preferably, the statistical significance of the overall goodness of fit is determined in order to determine the significance of the network model for representing the biological system. Optionally, the statistical significance of the assignment of individual cellular constituents to their best fitting classes is also determined.

Non-Parametric Statistics Methods

In order to determine the statistical significance of the overall goodness of fit, this invention preferably uses the methods of non-parametric statistics, since information concerning the distribution of possible values of F is not readily available. In particular, non-parametric methods are used to obtain a distribution of values of the overall goodness of fit, F, in case a null hypothesis is true, i.e., that the network model fits random input data. The actually determined goodness of fit is then compared to the distribution expected in case that this null distribution is true. The less likely that the actually observed or a more extreme goodness of fit is found in the distribution, the less likely the null hypothesis is true in this case and the more significant is the network model. Alternative models can thereby be ranked for fidelity to the data, thus avoiding biases introduced, e.g., by differing numbers of model parameters, or by changes in the influence matrix. According to the methods of Fisher (see, e.g., Conover, 2nd ed. 1980, *Practical Non-parametric Statistics,* section 5.11, John Wiley), the distribution can be simply and advantageously empirically obtained in the following manner.

First, the actually observed and measured data is randomly permuted with respect to the particular experiments that generated the data. In other words, the experiments, which compare changes in cellular constituents between two particular input states, are treated as returning data randomly selected from an experiment comparing other particular input states. This advantageously insures that the random input data has the same distributions of actual values as the actual input data. Next, the previous methods are used to determine the goodness of fit of the network model with respect to the random data. Finally, these steps are repeated for a sufficient number of time in order to obtain a sufficiently significant distribution (or histogram) of values of goodness of fit. It has been found in particular cases that between 500 and 2000 repetitions are usually sufficient.

In detail, these methods can be represented by the following methods. If the number of experiments is M, first, a random permutation, D, of the integers 1 ... M is found by methods of combinatorial programming known in the art. For example, Monte Carlo methods can be used to find such permutations. Then, the data observed for each cellular constituent is perturbed. If $x_{k,i}$ is the observed and measured data for the k'th cellular constituent in the i'th experiment, the randomized data, $x^P_{k,i}$ is given by the following equation.

$$x^{(p)}_{k,i} = x_{k,\Pi(i)} \quad (4)$$

Using the influence matrix, g, the output classes that best fit each observed cellular constituent are found. The output class best fitting the k'th cellular constituent is denoted $n^{(P)}(k)$. This overall goodness of fit to the randomized data, $F^{(P)}$, is be represented by the following equations, as previously.

$$F^{(p)} = \sum_k |g_{n^{(p)}(k)} * x^{(p)}_k| \quad (5)$$

$$F^{(p)} = \sum_k g_{n^{(p)}(k)} * |x^{(p)}_k|$$

A sufficient number of value of $F^{(P)}$ are determined in order to yield a histogram of the distribution, F, used to judge the significance of the actual goodness of fit. The fraction of such randomized $F^{(P)}$ that are greater than the actually determined F is significance, of P-value, of the network model.

Optionally, the significance with which individual cellular constituents are best fit with output classes can also be assessed. A first method for assessing the significance of the fit of a particular cellular constituent to the best fitting output class is substantially similar to the previous method for assessing the overall goodness of fit, and is applicable in the case where there are several, preferably at least 6, experiments used to test and confirm the network model. The significance of the actual goodness of fit of that cellular constituent is assessed in view of a distribution of the goodness of fit of that cellular constituent empirically determined from data similarly randomized as previously. The fraction of the data randomizations that have a better fit value than the actual value is the significance value. This is a similar method to that used for the overall P-value of the network model.

A second method for assessing the significance of the fit of a particular cellular constituent to the best fitting output class is applicable in the case where there are few experiments, preferably no more than 5, used to test and confirm the network model in the experiment set. In this case, the number of permutations is too small to obtain high significance values for the individual class assignments by the previous method. An estimate of the significance of class assignment can be obtained from parametric methods, for example by assuming prior knowledge of the magnitudes of the measurement errors, independent measurement errors from experiment to experiment, and a Gaussian error distribution.

In view of its definition in Section 5.2, the measure, x, of the changes in cellular constituents has unit variance. Since the rows of the influence matrix, $g_n$, are normalized also to have unit variance, the variance of the correlation, $g_n * x_k$, is equal to the number of experiments, N, in view of the prior assumptions. Thereby, a P-value can be assigned to the fit of the k'th cellular constituent to the n'th output class using the standard error function, denoted "erf".

$$p = \text{erf}\left(\frac{g_n * x_k}{N^{1/2}}\right) \quad (6)$$

With either method of assessing the significance of the it of a cellular constituent to an output class, it is often advantageous to determine P-values for assignments to multiple output classes. For example, the k'th cellular constituent can be assigned to the a'th output class with significance probability $P_a$, to the b'th output class with significance probability $P_b$, and so forth (these probabilities sum to unity).

The Maximum Likelihood Method

In embodiments of the invention where prior probability distributions can be estimated for a measure of change, x, the Maximum Likelihood method provides a powerful means for assessing the statistical significance of alternative network models without resorting to Monte Carlo randomizations. This method will be known to those of skill in the art (see, e.g., H L Van Trees, 1968, Detection Estimation and Modulation Theory, Vol I, Wiley and Sons). According to this approach, the possible influence matrix values (e.g., -1, 0, and +1) for element $g_{ni}$ are interpreted as distinct hypotheses, $H_{ni}$, for the behavior of genes of Class n in Experiment i. The likelihood of observing a series of change measures $x_{ki}$ across a series of experiments i=1 to M, assuming gene k is in Class n, is then $$L_{nk} = \prod_i P(x_{ki} | H_{ni}) \quad (7)$$

where $P(x|H)$ denotes the prior probability of observing x given the hypothesis H. Exemplary parametric probability distributions for the three-state case (change down, $H^-$, no change $H^0$, and change up $H^+$) are $$P(x_k | H^0) = \frac{1}{\sqrt{2\pi}\,\sigma_{k0}} \exp\left(-\frac{x_k^2}{2\sigma_{k0}^2}\right) \quad (8)$$

$$P(x_k | H^+) = \frac{1}{\sqrt{2\pi}\,\sigma_k} \exp\left(-\frac{(x_k - \mu_k)^2}{2\sigma_k^2}\right) \quad (9)$$

$$P(x_k | H^-) = \frac{1}{\sqrt{2\pi}\,\sigma_k} \exp\left(-\frac{(x_k + \mu_k)^2}{2\sigma_k^2}\right) \quad (10)$$

where $\mu_k$ and $\sigma_k$ are the mean value and standard deviation, respectively, of $x_{ki}$ predicted by the hypothesis $H^+$. $\sigma_{k0}$ is the standard deviation predicted by the null hypothesis, $H^0$. $\mu_k$, $\sigma_{k0}$, and $\sigma_k$ are estimated from repeated experiments in which x is known to change or is known not to change under the model.

Experiments in which all the model output classes are affected will provide estimates of $\mu_k$ and $\sigma_k$ even though the class assignments are unknown. Thus, in a preferred embodiment, the Maximum Likelihood method is used for network models having combinations of input states (i.e., differential experiments) that cause changes in all of the output classes. In a less preferred embodiment, experiments cannot be found for the network model that cause changes simultaneously in all of the output classes. In such an embodiment, the functional forms of $P(x|H^+)$ and $P(x|H^-)$ cannot be determined empirically. However, approximate forms may be assumed based on the typical behavior of x for those output classes which are known to change.

For example, in embodiments where x is defined according to Equation 2 in Section 5.2, above, the limiting values of x are +1/f and -1/f. Exemplary approximate probability distributions for $P(x|H^+)$ and $P(x|H^-)$ would then be the uniform distribution over the intervals [-1/f, 0] and [0, +1/f], respectively. The "0" end of these uniform distributions needs to be extended smoothly to allow for the contribution of measurement errors. This may be done, for example, by joining them with half of a Gaussian function, such as the function provided for $P(x|H^0)$ in Equation 8, above. Other possible approximate forms of probability distributions responding to prior knowledge of typical values of x in experiments where change is expected will be apparent to one of skill in the art.

The Maximum Likelihood method may also be generalized for the two-state situation, i.e., where the hypotheses are only no change, $H^0$, and change, $H^1$. Such a generalization will be apparent to one of skill in the art in view of the above taught examples.

Once the probability distribution, $P(x_{ki}|H)$, and likelihood, $L_{nk}$, have been determined, the class assignment, n(k), of the k'th cellular constituent is simply determined to be the class, n, which has the greatest (i.e., maximum) likelihood of observing the series of change measures $x_{ki}$, i.e., the operation $$\max_n \{L_{nk}\} \quad (11)$$

and the over-all model likelihood is $$L = \prod_k L_{n(k)k} \quad (12)$$

The preferred network model is then the one with the largest value of L.

5.4. CHOICE OF EFFICIENT EXPERIMENTS

This section describes methods for routinely and automatically choosing experiments with which to test and confirm a particular network model. These methods are, first, generally described, followed second, by an exemplary description of the preferred embodiment.

General Experimental Selection Methods

A network model according to this invention includes a input set of cellular constituents, a set of output classes, and logical relations linking the response of the output classes to perturbations or modifications to the input cellular constituents. Specifically, particular perturbations and/or modifications present or not present in the input set of cellular constituents are called the state of the input. Further, since experiments according to this invention observe relative changes in cellular constituents, they are defined by pairs of states.

The methods for choosing experiments involve two principal steps: a first step which chooses a covering set of input states that are sufficient to distinguish all output classes; and a second step which chooses experiments, defined by pairs of these states in the covering set, that are sufficient to experimentally distinguish all the output classes (also called "covering" pairs of input states). Concerning the first step, the covering states are chosen only from feasible states, which are those that can be experimentally realized. Typically, not all possible perturbations can be combined, and only those that can define the feasible input states. For example it may not be feasible to treat a cell simultaneously with two drugs which have an unwanted, perhaps toxic, interaction, or it may not be feasible to knock out more than one or two individual genes in a biological system, or so forth.

From the feasible states, a sufficient number of covering states is chosen to distinguish all the output classes. To distinguish a pair of output classes, states must be chosen that meet two criteria. A first criterion is that there is at least one chosen state for which the two output classes have different behaviors (if one is "0", the other is "1", or vice versa). The determination that the output classes have different behaviors can be made from, e.g., the network diagram, the logical relations, or the truth table of the network model.

In the case where logical inversion in the output classes behavior cannot be distinguished, which is the case where $|g*x|$ is used as the goodness of fit measure, a second and less apparent criterion is that there is at least one chosen state for which the two output classes have the same behavior. This criterion arises because, according to this case, two output classes which differ by a logical inversion cannot be actually distinguished. For example, an output class (i.e., a row of the influence matrix) with responses 0, 1, 1, 0, and 1 to five experiments cannot be distinguished from an output class with responses 1, 0, 0, 1, and 0. As a consequence, for each pair of output classes, there must also be a state in the covering set for which the output classes have the same behavior in order that logical inversion can be distinguished.

Preferably, where there are multiple possible choices, this selection of states is made to minimize some objective criterion of interest. In a preferred embodiment, costs are assigned to each input state, and the objective function is the sum of the costs of each state. For example, different perturbations or modifications can have different economic costs. Certain drugs may be notably more expensive than other drugs, gene deletions or knockouts may be inherently expensive, or so forth. Therefore, one objective criterion can be minimizing the total economic cost of creating all the selected states. Another objective criterion can be minimizing the total time required to create all the selected states. This invention is adaptable to any such objective criterion, which are preferably linear.

The choice of the set of covering sets can be made according to any algorithm known in the art for making choices minimizing an objective functions, including exhaustive search of all possible combinations of states. A preferred implementation according to the methods of linear programming is described subsequently.

Figure 9:
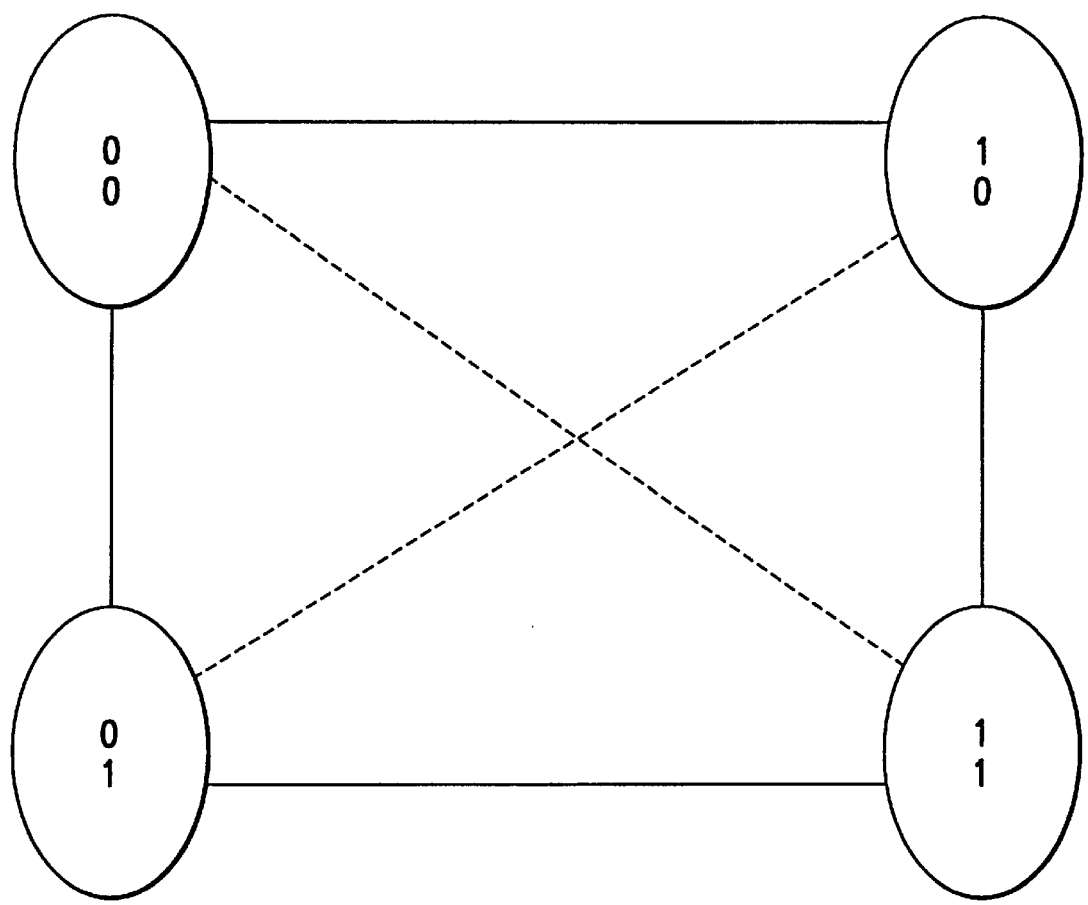
FIG. 9 illustrates selection of experiments for testing and confirming network models.

Concerning the second step, experiments are chosen as pairs of states from the covering set of states which are sufficient to experimentally distinguish all the output classes. A set of pairs of input states sufficient to experimentally distinguish all the pairs of output classes is called a "covering set of pairs of input states". Although experiments defined by all pairs of covering states are sufficient to distinguish all output classes, it is preferable to choose a minimum number of such pairs of covering states FIG. 9 illustrates all possible responses for two output classes responding to four input states. Each oval node in FIG. 9, which contains an indication of the response of a first output class positioned over an indication of the response of a second output class, corresponds to a separate input state. In the case where we cannot distinguish logical inversion in the model output classes behavior, in order to distinguish these two output classes, experiments must be defined either with a pair of states joined by the solid lines, or with both pairs of states joined by the dashed lines. In summary, to distinguish two output classes, either one experiment must be defined in which the two output classes have one of the following responses in the two states defining the experiment: (0, 0) vs. (1, 0), or (1, 0) vs. (1, 1), or (1, 1) vs. (0, 1), or (0, 1) vs. (0, 0). Alternately, two experiments must be defined in which the two output classes have the following responses: (0, 0) vs. (1, 1), and (1, 0) vs. (0, 1). In the case where we can distinguish logical inversion in the output classes behavior, only one of the dashed or solid lines in FIG. 9 is needed.

Preferably, where there are multiple possible choices for the experiments, the experiments are chosen which compare states which in total minimize the objective function of interest. Alternatively, the solution with the minimum number of experiments can be chosen.

As previously, the choice of the experiments can be made according to any algorithm known in the art for making choices minimizing an objective functions, including exhaustive search of all possible combinations of states. A preferred implementation according to the methods of linear programming is described subsequently.

Exemplary Description of the Preferred Embodiment

A preferred implementation of the above method using linear programming techniques is described next and exemplified with the network model illustrated in FIG. 2B. This implementation includes the following sequence of steps, each of which is described below.

(1) Determine the feasible input states.

(2) Assign costs to the input states.

(3) Generate input/output table derived from the network model.

(4) Generate first linear inequalities whose solution gives the set of covering states (those input states sufficient to distinguish the behavior of any pair of output classes).

(5) Solve the first linear inequalities.

(6) Generate second linear inequalities whose solution gives the experiments that can distinguish any pair of input states; the experiments are defined by pairs of input states found in step 5.

(7) Solve the second linear inequalities.

In the first step, experimentally feasible input states are selected from among all possible input states in view of the experimental techniques available in a particular implementation of this invention. Let the variable $\alpha=1, \ldots, M$, where there are M feasible input states. If there are N input cellular constituents, there can be at more $2^N$ feasible input states.

In the second step, each feasible input state is assigned a positive cost, $c_\alpha$, according to some objective cost function of interest.

In the third step, an input/output (truth) table is derived for the network as described in Section 5.1. Such a table can be created in a computer-implementation by standard combinatorial programming techniques. In the exemplary case of the network illustrated in FIG. 2B, the previous input/output table, Table 1, is repeated here for convenience as Table 8

TABLE 8

OUTPUT CLASSES OF FIG. 2B

| Output | $D = 0, P = 0$ | $D = 1, P = 0$ | $D = 0, P = 1$ | $D = 1, P = 1$ |
|---|---|---|---|---|
| Class | state 1 | state 2 | state 3 | state 4 |
| 1 | 0 | 1 | 0 | 1 |
| 2 | 0 | 0 | 1 | 0 |
| 3 | 0 | 0 | 0 | 1 |

Here all four states, states 1–4, are assumed to be feasible, and M=4.

In the fourth step, linear equalities are generated whose solution gives the set of covering states. To represent these inequalities, let the variable $x_\alpha$ be 1, if condition $\alpha$ is in the condition cover, and be 0 otherwise. Further, to represent the two criteria on states in order to distinguish output classes, let coefficients $SD_{ij\alpha}$ be 1 if output classes i and j have different behaviors in state $\alpha$, and be 0 otherwise; and let coefficients $SS_{ij\alpha}$ be 1 if output classes i and j have the same behaviors in state $\alpha$, and be 0 otherwise. Both coefficients SS and SD can be generated by routine examination of the input/output table. Then the linear programming problem whose solution give the set of covering states is:

Minimize the function:

$$\sum_{\alpha \in states} x_\alpha C_\alpha \qquad (13)$$

Subject to the constraints:

$$\sum_\alpha SD_{ij\alpha} x_\alpha \geq 1 \qquad (14)$$

$$\sum_\alpha SS_{ij\alpha} x_\alpha \geq 1$$

The sum in $\alpha$ is over all feasible states, and the indices i and j vary over all output classes with i>=j. For redundant coverings, which add robustness to the experimental determinations of goodness of fit, the right hand side of Equation 14 is set to an integer equal to two (double covering) or greater.

In the fifth step, Equations 13 and 14 are solved using methods well known to those of skill in the art. Linear inequalities such as equations 13 and 14 are well known in the art of linear optimization, and are routinely solved, e.g., to isolate faults in circuits in the context of test design for semiconductor electronics (see, e.g., Roth, 1980, Computer Logic, Testing and Verification, Computer Science Press; Stephan, Brayton, and Sangiovanni-Vincentelli, 1996, "Combinational Test Generation Using Satisfiability", IEEE Transactions on Computer-Aided Design of Integrated Circuits and Systems, 15:1167–1176; Bryan, 1992, "Symbolic Boolean Manipulation with Ordered Binary Decision Diagrams", ACM Computing Surveys, 24:293–318; and Bondya and Murty, 1976, Graph Theory with Applications, Macmillan: London, 1976).

In particular, it will be recognized by those of skill in the art that Equations 13 and 14 constitute a class of problems known as mixed-integer linear programming (MILP) problems. MILP problems may be solved by a variety of methods well known to those skilled in the art of mathematical optimization. In preferred embodiments, the MILP problem of this invention (i.e., the solution of Equations 13 and 14) is solved by an algorithm referred to herein as the branch-and-bound algorithm. Branch-and-bound algorithms are well known to those skilled in the art (see, e.g., Lawler and Wood, 1966, "Branch-and-Bound Methods: A Survey", OR, 14:699–719; Nemhauser and Wolsey, 1988, Integer and Combinatorial Optimization, Wiley, pp. 349–367; Papadimitriuos and Steiglitz, 1982, Combinatorial Optimization: Algorithms and Complexity, Prentice-Hall: Englewood Cliffs, N.J., pp. 433–453).

The branch-and-bound method is illustrated here in the context of Equations 13 and 14, and of exemplary Table 8. The following equations describe the set of covering states:

For output classes 1 & 2:

$$x_2+x_3+x_4 \geq 1 \qquad (a)$$

$$x_1 \geq 1 \qquad (b)$$

For output classes 1 & 3:

$$x_2 \geq 1 \qquad (c)$$

$$x_1+x_3+x_4 \geq 1 \qquad (d)$$

For output classes 2 & 3:

$$x_3+x_4 \geq 1 \qquad (e)$$

$$x_1+x_2 \geq 1 \qquad (f)$$

Solutions are explored in a branching structure starting always with the lowest-cost state, with the inequalities being solved in an order sorted by increasing number of variables. Thus the equations (a)–(f) above are solved in the order (b),(c),(e),(f),(a),(d). We begin by setting $x_1$=1 ($x_1$ "TRUE") to solve (b), then $x_2$=1($x_2$ "TRUE") to solve (c). These two conditions immediately solve (f). To solve (e) we can try either $x_3$=1 or $x_4$=1. This constitutes a branch in the search. We choose whichever is the lower-cost condition to try first. In this example, either choice solves (a) and (d) and we are done.

If the objective function Equation 13 is assumed to be $x_1+x_2+x_3+x_4$, reflecting the assumption of equal cost for each condition, then equations (a)–(f) have the following two solutions for the set of covering states: (1, 2, 3) and (1, 2, 4), corresponding to the two possible branches in the search. In general, it is only necessary to explore the lower-cost branch at the lowest level in the tree, since the total cost for any solution involving the other branches will always be higher.

In the sixth step, linear equalities are generated whose solution gives the experiments distinguishing all the output classes. To represent these inequalities, let variable $y_{\alpha\beta}$ be 1 if an experiment with the input state pair ($\alpha$, $\beta$) is defined, and be 0 otherwise. Further, to represent the criteria on experiments in order to distinguish output classes, let coefficients $E_{ij,\alpha\beta}$ be 1 if output classes i and j have the different behaviors in states $\alpha$ and $\beta$ that are permissible according to FIG. 9, and be 0 otherwise. Coefficients E can be generated by routine examination of the input/output table in view of the allowed experiments illustrated in FIG. 9 and listed in the description of that figure. Then the linear programming problem whose solution give the set of covering states is:

Minimize the function:

$$\sum_{\alpha,\beta \in states} y_{\alpha\beta}(C_\alpha + C_\beta) \quad (15)$$

Subject to the constraints:

$$\sum_{\alpha \geq \beta} E_{ij,\alpha\beta} y_{\alpha\beta} + \sum_{\alpha > \beta} \sum_{\gamma > \delta} E_{ij,\alpha\beta\gamma\delta} y_{\alpha\beta} y_{\gamma\delta} \geq 1 \quad (16)$$

The second term of Equation 16, above, allows for the combinations of input states represented by the dashed lines in FIG. 9. In analogy to the comments after Equation 14 above, double and higher coverings of experimental condition pairs can be sought be replacing the "1" on the right hand side of Equation 16 with "2" and larger integers. The sum in $\alpha$ and $\beta$ is over all feasible states, and the indices i and j vary over all output classes with i>=j. In other embodiments, alternative objective functions can be used as described above.

In the seventh step, equation 15 and 16 are solved by any method known in the art, such as the simplex algorithm or the preferred branch-and-bound search technique.

In view of equations 15 and 16, and of exemplary Table 8, the following equations describe the experiments for distinguishing the output classes.

For output classes 1 & 2:

$$y_{12}+y_{13}+y_{14}>=1$$

For output classes 1 & 3:

$$y_{13}+y_{14}+y_{23}+y_{24}>=1$$

For output classes 2 & 3:

$$y_{12}>=1$$

In the case where the covering states are selected to (1, 2, 3), a sufficient set of experiments consists of a first experiments comparing states 1 and 2 and a second experiment comparing states 1 and 3. In the case where the covering states are selected to (1, 2, 4), a sufficient set of experiments consists of a first experiments comparing states 1 and 2 and a second experiment comparing states 1 and 4.

5.5. EXPERIMENTAL TESTING TECHNIQUES

The experimental testing and confirmation of a network model described in Section 5.2 depends on the experimental modification or perturbation of cellular constituents input to the network model and the experimental measurement of the responses of the other cellular constituents in a cell or a biological system. For example, in one embodiment of the present invention, the modification of perturbation of input cellular constituents can be accomplished by exposure to specific drugs or by genetic manipulations, such as gene deletions, and the measurement of response of cellular constituents can be accomplished by gene expression technologies measuring mRNA (or cDNA derived therefrom) abundances.

This section sets out various experimental techniques for the required modification/perturbation and measurement. This invention is adaptable to these techniques and to others which accomplish the same results.

5.5.1. CELLULAR MODIFICATION METHODS

Methods for targeted modification and/or perturbation of cellular constituents that are input to biological network models at various levels of a cell are increasingly widely known and applied in the art. Any such methods that are capable of specifically targeting and modifying or perturbing cellular constituents can be employed in this invention. Saturating modification/perturbations cause the abundances (or the activities, or so forth) of cellular constituents to change between unmodified/unperturbed levels and modified/perturbed that are clearly distinct from the unmodified/unperturbed levels. Preferably, methods are employed that are also capable of controllably modifying or perturbing specific cellular constituents (e.g., gene expression, RNA concentrations, protein abundances, protein activities, or so forth). Controllable modifications/perturbations cause the abundances (or the activities, or so forth) of cellular constituents to undergo either a graded increase or a graded decrease through a plurality of controllable modified/perturbed levels. Of course, controllable modification/perturbation techniques can also be used in a saturating fashion.

The following methods are exemplary of those that can be used to modify cellular constituents and thereby to produce modification/perturbations of cellular constituents that are input to network models to be tested or confirmed. Preferable modification methods are capable of individually targeting each of a plurality of cellular constituents and most preferably a substantial fraction of such cellular constituents.

Biological network models are preferably tested or confirmed in cells of cell types derived from any organism for which genomic or expressed sequence information is available, and for which methods are available that permit saturating or controllable modification of the expression of specific genes. Genome sequencing is currently underway for several eukaryotic organisms, including humans, nematodes, Arabidopsis, and flies. In a preferred embodiment, the invention is carried out using a yeast, with *Saccharomyces cerevisiae* most preferred because the sequence of the entire genome of a *S. cerevisiae* strain has been determined. In addition, well-established methods are available for modifying or perturbing expression of yeast genes. A preferred strain of yeast is a *S. cerevisiae* strain for which yeast genomic sequence is known, such as strain S288C or substantially isogeneic derivatives of it (see, e.g., *Nature* 369, 371–8 (1994); *P.N.A.S.* 92:3809–13 (1995); *E.M.B.O. J.* 13:5795–5809 (1994), *Science* 265:2077–2082 (1994); *E.M.B.O. J.* 15:2031–49 (1996), all of which are incorporated herein. However, other strains may be used as well. Yeast strains are available from American Type Culture Collection, Rockville, Md. 20852. Standard techniques for manipulating yeast are described in C. Kaiser, S. Michaelis, & A. Mitchell, 1994, *Methods in Yeast Genetics: A Cold Spring Harbor Laboratory Course Manual,* Cold Spring Harbor Laboratory Press, New York; and Sherman et al., 1986, *Methods in Yeast Genetics: A Laboratory Manual,* Cold Spring Harbor Laboratory, Cold Spring Harbor. N.Y., both of which are incorporated by reference in their entirety and for all purposes.

Other advantages of yeast are that it is easily manipulable in the laboratory and that biological functions are often conserved between yeast and humans. For example, almost half of the proteins identified as defective in human heritable diseases show amino acid similarity to yeast proteins (Goffeau et al., 1996, Life with 6000 genes. *Science* 274:546–567).

The exemplary methods described in the following include use of titratable expression systems, use of transfection or viral transduction systems, direct modifications to RNA abundances or activities, use of saturating genetic modification/modification methods, direct modifications of protein abundances, and direct modification of protein activities including use of drugs (or chemical moieties in general) with specific known action.

Titratable Expression Systems

In a preferred embodiment wherein yeast is employed, any of the several known titratable, or equivalently controllable, expression systems available for use in the budding yeast *Saccharomyces cerevisiae* are adaptable to this invention (Mumberg et al., 1994, Regulatable promoter of *Saccharomyces cerevisiae*: comparison of transcriptional activity and their use for heterologous expression, Nucl. Acids Res. 22:5767–5768). Usually, gene expression is controlled by transcriptional controls, with the promoter of the gene to be controlled replaced on its chromosome by a controllable, exogenous promoter. The most commonly used controllable promoter in yeast is the GAL1 promoter (Johnston et al., 1984, Sequences that regulate the divergent GAL1–GAL10 promoter in *Saccharomyces cerevisiae*, Mol Cell. Biol. 8:1440–1448). The GAL1 promoter is strongly repressed by the presence of glucose in the growth medium, and is gradually switched on in a graded manner to high levels of expression by the decreasing abundance of glucose and the presence of galactose. The GAL1 promoter usually allows a 5–100 fold range of expression control on a gene of interest.

Other frequently used promoter systems include the MET25 promoter (Kerjan et al., 1986, Nucleotide sequence of the *Saccharomyces cerevisiae* MET25 gene, Nucl. Acids. Res. 14:7861–7871), which is induced by the absence of methionine in the growth medium, and the CUP1 promoter, which is induced by copper (Mascorro-Gallardo et al., 1996, Construction of a CUP1 promoter-based vector to modulate gene expression in *Saccharomyces cerevisiae*, Gene 172:169–170). All of these promoter systems are controllable in that gene expression can be incrementally controlled by incremental changes in the abundances of a controlling moiety in the growth medium.

One disadvantage of the above listed expression systems is that control of promoter activity (effected by, e.g., changes in carbon source, removal of certain amino acids), often causes other changes in cellular physiology which independently alter the expression levels of other genes. A recently developed system for yeast, the Tet system, alleviates this problem to a large extent (Gari et al., 1997, A set of vectors with a tetracycline-regulatable promoter system for modulated gene expression in *Saccharomyces cerevisiae*, Yeast 13:837–848). The Tet promoter, adopted from mammalian expression systems (Gossen et al., 1995, Transcriptional activation by tetracyclines in mammalian cells, Proc. Nat. Acad. Sci. USA 89:5547–5551) is modulated by the concentration of the antibiotic tetracycline or the structurally related compound doxycycline. Thus, in the absence of doxycycline, the promoter induces a high level of expression, and the addition of increasing levels of doxycycline causes increased repression of promoter activity. Intermediate levels gene expression can be achieved in the steady state by addition of intermediate levels of drug. Furthermore, levels of doxycycline that give maximal repression of promoter activity (10 micrograms/ml) have no significant effect on the growth rate on wild type yeast cells (Gari et al., 1997, A set of vectors with a tetracycline-regulatable promoter system for modulated gene expression in *Saccharomyces cerevisiae*, Yeast 13:837–848).

In mammalian cells, several means of titrating expression of genes are available (Spencer, 1996, Creating conditional mutations in mammals, Trends Genet. 12:181–187). As mentioned above, the Tet system is widely used, both in its original form, the "forward" system, in which addition of doxycycline represses transcription, and in the newer "reverse" system, in which doxycycline addition stimulates transcription (Gossen et al., 1995, Transcriptional activation by tetracyclines in mammalian cells, Proc. Nat. Acad. Sci. USA 89:5547–5551; Hoffmann et al., 1997, A novel tetracycline-dependent expression vector with low basal expression and potent regulatory properties in various mammalian cell lines, Nucl. Acids. Res. 25:1078–1079). Another commonly used controllable promoter system in mammalian cells is the ecdysone-inducible system developed by Evans and colleagues (No et al., 1996, Ecdysone-inducible gene expression in mammalian cells and transgenic mice, Proc. Nat. Acad. Sci. USA 93:3346–3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Controlling protein association and subcellular localization with a synthetic ligand that induces heterodimerization of proteins, Proc. Nat. Acad. Sci. USA 93:4604–4607; Spencer, 1996, Creating conditional mutations in mammals, Trends Genet. 12:181–187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

For each of the mammalian expression systems described above, as is widely known to those of skill in the art, the gene of interest is put under the control of the controllable promoter, and a plasmid harboring this construct along with an antibiotic resistance gene is transfected into cultured mammalian cells. In general, the plasmid DNA integrates into the genome, and drug resistant colonies are selected and screened for appropriate expression of the regulated gene. Alternatively, the regulated gene can be inserted into an episomal plasmid such as pCEP4 (Invitrogen, Inc.), which contains components of the Epstein-Barr virus necessary for plasmid replication.

In a preferred embodiment, titratable expression systems, such as the ones described above, are introduced for use into cells or organisms lacking the corresponding endogenous gene and/or gene activity, e.g., organisms in which the endogenous gene has been disrupted or deleted. Methods for producing such "knock outs" are well known to those of skill in the art, see e.g., Pettitt et al., 1996, Natl. Acad. Sci. USA 92:10824–10830; Ramirez-Solis et al., 1993, Methods Enzymol. 225: 855–878; and Thomas et al., 1987, Cell 51:503–512.

Transfection Systems for Mammalian Cells

Transfection or viral transduction of target genes can introduce controllable perturbations in cellular constituents in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1+/− system (Invitrogen, Inc.) or retroviral vectors, and introduced into the non-expressing host cells. Transfected or transduced cells expressing the target gene may be isolated by selection for a drug resistance marker encoded by the expression vector. The gene transcription level is a monotonic function of the transfection dosage. In this way, the effects of varying levels of the target gene may be investigated.

A particular example of the use of this method is the search for drugs that target the src-family protein tyrosine kinase, lck, a key component of the T cell receptor activation pathway (Anderson et al., 1994, Involvement of the protein tyrosine kinase p56 (lck) in T cell signaling and thymocyte development, Adv. Immunol. 56:171–178). Inhibitors of this enzyme are of interest as potential immunosuppressive drugs (Hanke J H, 1996, Discovery of a Novel, Potent, and src family-selective tyrosine kinase inhibitor, J. Biol Chem 271(2):695–701). A specific mutant of the Jurkat T cell line (JcaM1) is available that does not express lck kinase (Straus et al., 1992, Genetic evidence for the involvement of the lck tyrosine kinase in signal transduction through the T cell antigen receptor, Cell 70:585–593). Therefore, introduction of the lck gene into JCaM1 by transfection or transduction permits specific perturbation of network models of T cell activation regulated by the lck kinase. Since the efficiency of transfection or transduction is dose related, this methods leads to controllable (or saturating) modifications or perturbations. This method is generally useful for providing perturbations of gene expression or protein abundances in cells not normally expressing the genes to be perturbed.

Saturating Modification/modification Methods

Saturating modifications/perturbations can be accomplished with genetic modification techniques, such as gene deletion or disruption. In a preferred embodiment, such genetic techniques are carried out using a yeast, with *Saccharomyces cerevisiae* most preferred because the sequence of the entire genome of a *S. cerevisiae* strain has been determined. Well-established methods for deleting or otherwise disrupting or modifying specific genes are available in yeast, and are described herein. Further, it is believed that most of the genes in *S. cerevisiae* can be deleted, one at a time, with little or no effect on the ability of the organism to reproduce.

In one embodiment, yeast genes are disrupted or deleted using the method of Baudin et al., 1993, A simple and efficient method for direct gene deletion in *Saccharomyces cerevisiae, Nucl. Acids Res.* 21:3329–3330, which is incorporated by reference in its entirety for all purposes. This method uses a selectable marker, e.g., the KanMx gene, which serves in a gene replacement cassette. The cassette is transformed into a haploid yeast strain and homologous recombination results in the replacement of the targeted gene (ORF) with the selectable marker. In one embodiment, a precise null mutation (a deletion from start codon to stop codon) is generated. Also see, Wach et al., 1994, New heterologous modules for classical or PCR-based gene disruptions in *Saccharomyces cerevisiae, Yeast* 10:1793–1808; Rothstein, 1991, *Methods Enzymol.* 194:281 each of which is incorporated by reference in its entirety for all purposes. An advantage to using precise null mutants is that it avoids problems with residual or altered functions associated with truncated products.

However, in some embodiments a deletion or mutation affecting less than the entire protein coding sequence, e.g., a deletion of only one domain of a protein having multiple domains and multiple activities, is used. It some embodiments, the polynucleotide (e.g., containing a selectable marker) used for transformation of the yeast includes an oligonucleotide marker that serves as a unique identifier of the resulting deletion strain as described, for example, in Shoemaker et al., 1996, *Nature Genetics* 14:450. Once made, disruptions can be verified by PCR using the internal KanMx sequences, and an external primer in the yeast genome that immediately flanks the disrupted open reading frame and assaying for a PCR product of the expected size. When yeast is used, it may sometimes be advantageous to disrupt ORFs in three yeast strains, i.e., haploid strains of the a and á mating types, and a diploid strain (for deletions of essential genes).

Over-expression mutants are preferably made by modifying the promoter for the gene of interest, usually by replacing the promoter with a promoter other than that naturally associated with the gene, such as an inducible promoter. In addition, or alternatively, an enhancer sequence can be added or modified. Methods for carrying out genetic modification to increase expression from a predetermined gene are well known in the art. Such methods include expression for vectors, such as plasmids, carrying the gene of interest.

In addition to yeast cells, the methods of the present invention can be carried out using cells from any eukaryote for which genomic sequence of at least one gene is available (or becomes available in the future), e.g., fruit flies (e.g., *D. melanogaster*), nematodes (e.g., *C. elegans*), and mammalian cells such as cells derived from mice and humans. For example, more than 60% of the *C. elegans* genome has been sequenced ("Experts gather to discuss technologies being developed for functional genomic analysis," *Genetic Engineering News:*16, Nov. 15, 1996). Methods for disruption of specific genes are well known to those of skill, see, e.g., Anderson, 1995, Methods Cell Biol. 48:31; Pettitt et al., 1996, Development 122:4149–4157; Spradling et al., 1995, Proc. Natl. Acad. Sci. USA; Ramirez-Solis et al., 1993, Methods Enzymol. 225:855; and Thomas et al., 1987, Cell 51:503, each of which is incorporated herein by reference in its entirety for all purposes. For example, targeted deletion of individual genes has been described in murine systems (Mortensen et al., 1992, Production of homozygous mutant ES cells with a single targeting construct, Mol. Cell. Biol. 12:2391–2395).

Methods of Modifying RNA Abundances or Activities

Methods of modifying RNA abundances and activities currently fall within three classes, ribozymes, antisense species, and RNA aptamers (Good et al., 1997, Gene Therapy 4: 45–54). Controllable application or exposure of a cell to these entities permits controllable perturbation of RNA abundances.

Ribozymes are RNAs which are capable of catalyzing RNA cleavage reactions (Cech, 1987, Science 236:1532–1539; PCT International Publication WO 90/11364, published Oct. 4, 1990; Sarver et al., 1990, Science 247: 1222–1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA (Haseloff et al., 1988, Nature 334:585–591; Koizumi et al., 1988, FEBS Lett., 228:228–230; Koizumi et al., 1988, FEBS Lett., 239:285–288). Ribozyme methods involve exposing a cell to, inducing expression in a cell, etc. of such small RNA ribozyme molecules (Grassi and Marini, 1996, Annals of Medicine 28: 499–510; Gibson, 1996, Cancer and Metastasis Reviews 15: 287–299).

Ribozymes can be routinely expressed in vivo in sufficient number to be catalytically effective in cleaving mRNA, and thereby modifying mRNA abundances in a cell (Cotten et al., 1989, Ribozyme mediated destruction of RNA in vivo, The EMBO J. 8:3861–3866). In particular, a ribozyme coding DNA sequence, designed according to the previous rules and synthesized, for example, by standard phosphoramidite chemistry, can be ligated into a restriction enzyme site in the anticodon stem and loop of a gene encoding a tRNA, which can then be transformed into and expressed in a cell of interest by methods routine in the art. Preferably, an inducible promoter (e.g., a glucocorticoid or a tetracycline esponse element) is also introduced into this construct so that ribozyme expression can be selectively controlled. For saturating use, a highly and constituently active promoter can be used. tDNA genes (i.e., genes encoding tRNAs) are useful in this application because of their small size, high rate of transcription, and ubiquitous expression in different kinds of tissues. Therefore, ribozymes can be routinely designed to cleave virtually any mRNA sequence, and a cell can be routinely transformed with DNA coding for such ribozyme sequences such that a controllable and catalytically effective amount of the ribozyme is expressed. Accordingly the abundance of virtually any RNA species in a cell can be modified or perturbed.

In another embodiment, activity of a target RNA (preferable MRNA) species, specifically its rate of translation, can be controllably inhibited by the controllable application of antisense nucleic acids. Application at high levels results in a saturating inhibition. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553–6556; Lemaitre et al., 1987, Proc. Natl. Acad. Sci. 84: 648–652; PCT Publication No. WO 88/09810, published Dec. 15, 1988), hybridization-triggered cleavage agents (see, e.g., Krol et al., 1988, BioTechniques 6: 958–976) or intercalating agents (see, e.g., Zon, 1988, Pharm. Res. 5: 539–549).

In a preferred aspect of the invention, an antisense oligonucleotide is provided, preferably as single-stranded DNA. The oligonucleotide may be modified at any position on its structure with constituents generally known in the art.

The antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-á-anomeric oligonucleotide. An á-anomeric oligonucleotide forms specific double-stranded hybrids with complementary RNA in which, contrary to the usual B-units, the strands run parallel to each other (Gautier et al., 1987, Nucl. Acids Res. 15: 6625–6641).

The oligonucleotide may be conjugated to another molecule, e.g., a peptide, hybridization triggered cross-linking agent, transport agent, hybridization-triggered cleavage agent, etc.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still torm a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16: 3209), methylphosphonate oligonucleotides can be prepared by use of controlled pore glass polymer supports (Sarin et al., 1988, Proc. Natl. Acad. Sci. U.S.A. 85: 7448–7451), etc. In another embodiment, the oligonucleotide is a 2'-0-methylribonucleotide (Inoue et al., 1987, Nucl. Acids Res. 15: 6131–6148), or a chimeric RNA-DNA analog (Inoue et al., 1987, FEBS Lett. 215: 327–330).

The synthesized antisense oligonucleotides can then be administered to a cell in a controlled or saturating manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. If the expression is controlled to be at a high level, a saturating perturbation or modification results. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Other usable promoters for mammalian cells include, but are not limited to: the SV40 early promoter region (Bernoist and Chambon, 1981, Nature 290: 304–310), the promoter contained in the 3' long terminal repeat of Rous sarcoma virus (Yamamoto et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42), etc.

Therefore, antisense nucleic acids can be routinely designed to target virtually any mRNA sequence, and a cell can be routinely transformed with or exposed to nucleic acids coding for such antisense sequences such that an effective and controllable or saturating amount of the antisense nucleic acid is expressed. Accordingly the translation of virtually any RNA species in a cell can be modified or perturbed.

Finally, in a further embodiment, RNA aptamers can be introduced into or expressed in a cell. RNA aptamers are specific RNA ligands for proteins, such as for Tat and Rev RNA (Good et al., 1997, Gene Therapy 4: 45–54) that can specifically inhibit their translation.

Methods of Modifying Protein Abundances

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et al., 1994, Science 263:1273–1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell,* W. H. Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. This technique also permits controllable modification of degradation rates since heat activation of degradation is controllably blocked by exposure methotrexate. This method is adaptable to other N-terminal degrons which are responsive to other inducing factors, such as drugs and temperature changes.

Target protein activities can also be decreased by (neutralizing) antibodies. By providing for controlled or saturating exposure to such antibodies, protein abundances/activities can be modified or perturbed in a controlled or saturating manner. For example, antibodies to suitable epitopes on protein surfaces may decrease the abundance, and thereby indirectly decrease the activity, of the wild-type active form of a target protein by aggregating active forms into complexes with less or minimal activity as compared to the wild-type unaggregated wild-type form. Alternately, antibodies may directly decrease protein activity by, e.g., interacting directly with active sites or by blocking access of substrates to active sites. Conversely, in certain cases, (activating) antibodies may also interact with proteins and their active sites to increase resulting activity. In either case, antibodies (of the various types to be described) can be raised against specific protein species (by the methods to be described) and their effects screened. The effects of the antibodies can be assayed and suitable antibodies selected that raise or lower the target protein species concentration and/or activity. Such assays involve introducing antibodies into a cell (see below), and assaying the concentration of the wild-type amount or activities of the target protein by standard means (such as immunoassays) known in the art. The net activity of the wild-type form can be assayed by assay means appropriate to the known activity of the target protein.

Antibodies can be introduced into cells in numerous fashions, including, for example, microinjection of antibodies into a cell (Morgan et al., 1988, Immunology Today 9:84–86) or transforming hybridoma mRNA encoding a desired antibody into a cell (Burke et al., 1984, Cell 36:847–858). In a further technique, recombinant antibodies can be engineering and ectopically expressed in a wide variety of non-lymphoid cell types to bind to target proteins as well as to block target protein activities (Biocca et al., 1995, Trends in Cell Biology 5:248–252). Expression of the antibody is preferably under control of a controllable promoter, such as the Tet promoter, or a constitutively active promoter (for production of saturating perturbations). A first step is the selection of a particular monoclonal antibody with appropriate specificity to the target protein (see below). Then sequences encoding the variable regions of the selected antibody can be cloned into various engineered antibody formats, including, for example, whole antibody, Fab fragments, Fv fragments, single chain Fv fragments ($V_H$ and $V_L$ regions united by a peptide linker) ("ScFv" fragments), diabodies (two associated ScFv fragments with different specificities), and so forth (Hayden et al., 1997, Current Opinion in Immunology 9:210–212). Intracellularly expressed antibodies of the various formats can be targeted into cellular compartments (e.g., the cytoplasm, the nucleus, the mitochondria, etc.) by expressing them as fusions with the various known intracellular leader sequences (Bradbury et al., 1995, *Antibody Engineering* (vol. 2) (Borrebaeck ed.), pp. 295–361, IRL Press). In particular, the ScFv format appears to be particularly suitable for cytoplasmic targeting.

Antibody types include, but are not limited to, polyclonal, monoclonal, chimeric, single chain, Fab fragments, and an Fab expression library. Various procedures known in the art may be used for the production of polyclonal antibodies to a target protein. For production of the antibody, various host animals can be immunized by injection with the target protein, such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacillus Calmette-Guerin (BCG) and corynebacterium parvum.

For preparation of monoclonal antibodies directed towards a target protein, any technique that provides for the production of antibody molecules by continuous cell lines in culture may be used. Such techniques include, but are not restricted to, the hybridoma technique originally developed by Kohler and Milstein (1975, Nature 256: 495–497), the trioma technique, the human B-cell hybridoma technique (Kozbor et al., 1983, Immunology Today 4: 72), and the EBV hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. USA 80: 2026–2030), or by transforming human B cells with EBV virus in vitro (Cole et al., 1985, in *Monoclonal Antibodies and Cancer Therapy*, Alan R. Liss, Inc., pp. 77–96). In fact, according to the invention, techniques developed for the production of "chimeric antibodies" (Morrison et al., 1984, Proc. Natl. Acad. Sci. USA 81: 6851–6855; Neuberger et al., 1984, Nature 312:604–608; Takeda et al., 1985, Nature 314: 452–454) by splicing the genes from a mouse antibody molecule specific for the target protein together with genes from a human antibody molecule of appropriate biological activity can be used; such antibodies are within the scope of this invention.

Additionally, where monoclonal antibodies are advantageous, they can be alternatively selected from large antibody libraries using the techniques of phage display (Marks et al., 1992, J. Biol. Chem. 267:16007–16010). Using this technique, libraries of up to $10^{12}$ different antibodies have been expressed on the surface of fd filamentous phage, creating a "single pot" in vitro immune system of antibodies available for the selection of monoclonal antibodies (Griffiths et al., 1994, EMBO J. 13:3245–3260). Selection of antibodies from such libraries can be done by techniques known in the art, including contacting the phage to immobilized target protein, selecting and cloning phage bound to the target, and subcloning the sequences encoding the antibody variable regions into an appropriate vector expressing a desired antibody format.

According to the invention, techniques described for the production of single chain antibodies (U.S. Pat. No. 4,946,778) can be adapted to produce single chain antibodies specific to the target protein. An additional embodiment of the invention utilizes the techniques described for the construction of Fab expression libraries (Huse et al., 1989, Science 246: 1275–1281) to allow rapid and easy identification of monoclonal Fab fragments with the desired specificity for the target protein.

Antibody fragments that contain the idiotypes of the target protein can be generated by techniques known in the art. For example, such fragments include, but are not limited to: the $F(ab')_2$ fragment which can be produced by pepsin digestion of the antibody molecule; the Fab' fragments that can be generated by reducing the disulfide bridges of the $F(ab')_2$ fragment, the Fab fragments that can be generated by treating the antibody molecule with papain and a reducing agent, and Fv fragments.

In the production of antibodies, screening for the desired antibody can be accomplished by techniques known in the art, e.g., ELISA (enzyme-linked immunosorbent assay). To select antibodies specific to a target protein, one may assay generated hybridomas or a phage display antibody library for an antibody that binds to the target protein.

Methods of Modifying Protein Activities

Methods of directly modifying protein activities include, inter alia, dominant negative mutations, specific drugs or chemical moieties, and also the use of antibodies, as previously discussed.

Dominant negative mutations are mutations to endogenous genes or mutant exogenous genes that when expressed in a cell disrupt the activity of a targeted protein species. Depending on the structure and activity of the targeted protein, general rules exist that guide the selection of an appropriate strategy for constructing dominant negative mutations that disrupt activity of that target (Hershkowitz, 1987, Nature 329:219–222). In the case of active monomeric forms, over expression of an inactive form can cause competition for natural substrates or ligands sufficient to significantly reduce net activity of the target protein. Such over expression can be achieved by, for example, associating a promoter, preferably a controllable or inducible promoter, or also a constitutively expressed promoter, of increased activity with the mutant gene. Alternatively, changes to active site residues can be made so that a virtually irreversible association occurs with the target ligand. Such can be achieved with certain tyrosine kinases by careful replacement of active site serine residues (Perlmutter et al., 1996, Current Opinion in Immunology 8:285–290).

In the case of active multimeric forms, several strategies can guide selection of a dominant negative mutant. Multimeric activity can be decreased in a controlled or saturating manner by expression of genes coding exogenous protein fragments that bind to multimeric association domains and prevent multimer formation. Alternatively, controllable or saturating over expression of an inactive protein unit of a particular type can tie up wild-type active units in inactive multimers, and thereby decrease multimeric activity (Nocka et al., 1990, The EMBO J. 9:1805–1813). For example, in the case of dimeric DNA binding proteins, the DNA binding domain can be deleted from the DNA binding unit, or the activation domain deleted from the activation unit. Also, in this case, the DNA binding domain unit can be expressed without the domain causing association with the activation unit. Thereby, DNA binding sites are tied up without any possible activation of expression. In the case where a particular type of unit normally undergoes a conformational change during activity, expression of a rigid unit can inactivate resultant complexes. For a further example, proteins involved in cellular mechanisms, such as cellular motility, the mitotic process, cellular architecture, and so forth, are typically composed of associations of many subunits of a few types. These structures are often highly sensitive to disruption by inclusion of a few monomeric units with structural defects. Such mutant monomers disrupt the relevant protein activities and can be expressed in a cell in a controlled or saturating manner.

In addition to dominant negative mutations, mutant target proteins that are sensitive to temperature (or other exogenous factors) can be found by mutagenesis and screening procedures that are well-known in the art.

Also, one of skill in the art will appreciate that expression of antibodies binding and inhibiting a target protein can be employed as another dominant negative strategy.

Drugs of specific known action

Finally, activities of certain target proteins can be modified or perturbed in a controlled or a saturating manner by exposure to exogenous drugs or ligands. Since the methods of this invention are often applied to testing or confirming biological network models of the pathways of drug action, drug exposure is an important method of modifying/perturbing cellular constituents input to network models. In a preferred embodiment, input cellular constituents are perturbed either by drug exposure or genetic manipulation (such as gene deletion or knockout) and system responses are measured by gene expression technologies (such as hybridization to gene transcript arrays, described in the following).

In a preferable case, a drug is known that interacts with only one target protein in the cell and alters the activity of only that one target protein, either increasing or decreasing the activity. Graded exposure of a cell to varying amounts of that drug thereby causes graded perturbations of network models having that target protein as an input. Saturating exposure causes saturating modification/perturbation. For example, Cyclosporin A is a very specific regulator of the calcineurin protein, acting via a complex with cyclophilin. A titration series of Cyclosporin A therefore can be used to generate any desired amount of inhibition of the calcineurin protein. Alternately, saturating exposure to Cyclosporin A will maximally inhibit the calcineurin protein.

Less preferably, a drug is known and used that alters the activity of only a few (e.g., 2–5) target proteins with separate, distinguishable, and non-overlapping effects. Graded (or saturating) exposure to such a drug causes graded (or saturating) perturbations to the, perhaps, several network models that have those proteins as input.

In the case of yeast, it is preferable to harvest the yeast in early log phase, since expression patterns are relatively insensitive to time of harvest at that time. The drug is added is a graded amount that depends on the particular characteristics of the drug, but usually will be between about 1 ng/ml and 100 mg/ml. In some cases a drug will be solubilized in a solvent such as DMSO.

In the case where the methods of this invention are used to model the pathway of drug action in a biological system, preferably, a saturating level of drug exposure is used which produces clear responses from the largest number of cellular constituents (e.g., as measured in the transcriptional state of a cell) without causing substantial toxicities or growth defects (in the case of cell cultures). This is because, the response of a biological system to drug exposure in terms of number of cellular constituents effected beyond any fixed threshold increases with the level of drug exposure. For any single pathway of drug action, the identities of the cellular constituents affected are substantially constant, while the magnitude of the effect increases with exposure level. However, at higher exposure levels, more cellular pathways are effected, and therefore more cellular constituents are effected. This behavior has been confirmed over a range of exposures for drugs such as methotrexate, FK506, Cyclosporin A, and Trichostatin. Therefore, the best fitting network models of drug action typically changes with drug concentration, and the highest practical concentrations are preferably used in order to elucidate the full spectrum of drug actions.

5.5.2. MEASUREMENT METHODS

The experimental testing and confirmation methods of this invention also depend of measurements of responses of cellular constituents (other than those in the network model) in response to modifications/perturbations of the cellular constituents input to the model. The cellular constituents measured can be from any aspect of the biological state of a cell. They can be from the transcriptional state, in which RNA abundances are measured, the translation state, in which protein abundances are measured, the activity state, in which protein activities are measured. The cellular characteristics can also be from mixed aspects, for example, in which the activities of one or more proteins are measured along with the RNA abundances (gene expressions) of other cellular constituents. This section describes exemplary methods for measuring the cellular constituents in drug or pathway responses. This invention is adaptable to other methods of such measurement.

Preferably, in this invention the transcriptional state of the other cellular constituents are measured. The transcriptional state can be measured by techniques of hybridization to arrays of nucleic acid or nucleic acid mimic probes, described in the next subsection, or by other gene expression technologies, described in the subsequent subsection. However measured, the result is response data including values representing RNA abundance ratios, which usually reflect DNA expression ratios (in the absence of differences in RNA degradation rates).

In various alternative embodiments of the present invention, aspects of the biological state other than the transcriptional state, such as the translational state, the activity state, or mixed aspects can be measured.

In all embodiments, measurements of the cellular constituents should be made in a manner that is relatively independent of when the measurement are made. In yeast, for example, it has been shown that (DeRisi et al., 1997, Exploring the metabolic and genetic control of gene expression on a genomic scale, Science 278: 680–686) in early log phase expression patterns are relatively insensitive to time of harvest. Therefor, preferably, yeast cells are harvested for measurements at one or two times in early log phase so that measurement time is not a variable.

5.5.2.1 TRANSCRIPTIONAL STATE MEASUREMENT

Preferably, measurement of the transcriptional state is made by hybridization to transcript arrays, which are described in this subsection. Certain other methods of transcriptional state measurement are described later in this subsection.

Transcript Arrays Generally

In a preferred embodiment the present invention makes use of "transcript arrays" (also called herein "microarrays"). Transcript arrays can be employed for analyzing the transcriptional state in a cell, and especially for measuring the transcriptional states of a cells exposed to graded levels of a drug of interest or to graded modifications/perturbations to cellular constituents input to a biological network model.

In one embodiment, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will specifically bind the product of a single gene in the cell. Although there may be more than one physical binding site (hereinafter "site") per specific mRNA, for the sake of clarity the discussion below will assume that there is a single site. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses one cell is exposed to a drug and another cell of the same type is not exposed to the drug. In the case of responses to modifications/perturbations to cellular constituents input to a network model, one cell is exposed to such modifications/perturbations and another cell of the same type is not exposed to the pathway perturbation. Generally, since experiments for testing or confirming biological network models typically include comparisons between two states of the input to the network model, preferably one cell is exposed to one state of the input cellular constituents and the other cell is exposed to the other state of the input cellular constituents. The cDNA derived from each of the two cell types are differently labeled so that they can be distinguished. In one embodiment, for example, cDNA from a cell treated with a drug (or exposed to a modification/perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each CDNA set is determined for each site on the array, and any relative difference in abundance of a particular mRNA detected.

In the example described above, the cDNA from the drug-treated (or modified/perturbed) cell will fluoresce green when the fluorophore is stimulated and the cDNA from the untreated cell will fluoresce red. As a result, when the drug treatment (or modification/perturbation) has no effect, either directly or indirectly, on the relative abundance of a particular mRNA in a cell, the mRNA will be equally prevalent in both cells and, upon reverse transcription, red-labeled and green-labeled cDNA will be equally prevalent. When hybridized to the microarray, the binding site(s) for that species of RNA will emit wavelengths characteristic of both fluorophores (and appear brown in combination). In contrast, when the drug-exposed (or modified/perturbed) cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, Quantitative monitoring of gene expression patterns with a complementary DNA microarray, Science 270:467–470, which is incorporated by reference in its entirety for all purposes. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

Preferably, gene expression data is combined from repeated experiments to reduce and characterize the randomly occurring experimental errors. Such a characterization leads to an estimate of the additive experimental error term, ó, in Equation 2. Further, reversing the fluorescent labels in pairs of two-color differential hybridization experiments advantageously permits reduction in fluorescent-label-dependent and color-dependent biases peculiar to individual genes, array spot locations, experimental protocols, and observation equipment. Characterization of these biases leads to an estimate of the multiplicative experimental error term, f, in Equation 2.

Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site"

(hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to testing and confirming a biological network model of interest. A "gene" is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, *Science* 274:546–567, which is incorporated by reference in its entirety for all purposes). In contrast, the human genome is estimated to contain approximately $10^5$ genes.

Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., *Oligo pl version* 5.0 (National Biosciences). In the case of binding sites corresponding to very long genes, it will sometimes be desirable to amplify segments near the 3' end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, *PCR Protocols: A Guide to Methods and Applications,* Academic Press Inc. San Diego, Calif., which is incorporated by reference in its entirety for all purposes. It will be apparent that computer controlled robotic systems are useful for isolating and amplifying nucleic acids.

An alternative means for generating the nucleic acid for the microarray is by synthesis of synthetic polynucleotides or oligonucleotides, e.g., using N-phosphonate or phosphoramidite chemistries (Froehler et al., 1986, *Nucleic Acid Res* 14:5399–5407; McBride et al., 1983, *Tetrahedron Lett.* 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, *Nature* 365:566–568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, *Genomics* 29:207–209). In yet another embodiment, the polynucleotide of the binding sites is RNA.

Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary DNA microarray, *Science* 270:467–470. This method is especially useful for preparing microarrays of cDNA. See also DeRisi et al., 1996, Use of a cDNA microarray to analyze gene expression patterns in human cancer, *Nature Genetics* 14:457–460; Shalon et al., 1996, A DNA microarray system for analyzing complex DNA samples using two-color fluorescent probe hybridization, *Genome Res.* 6:639–645; and Schena et al., 1995, Parallel human genome analysis; microarray-based expression of 1000 genes, *Proc. Natl. Acad. Sci. USA* 93:10539–11286. Each of the aforementioned articles is incorporated by reference in its entirety for all purposes.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767–773; Pease et al., 1994, Light-directed oligonucleotide arrays for rapid DNA sequence analysis, *Proc. Natl. Acad. Sci. USA* 91:5022–5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, *Biosensors & Bioelectronics* 11: 687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids Res.*

20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller.

Generating Labeled Probes

Methods for preparing total and poly(A) $^+$RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). Poly(A) $^+$RNA is selected by selection with oligo-dT cellulose (see Sambrook et al., supra). Cells of interest include wild-type cells, drug-exposed wild-type cells, cells with modified/perturbed cellular constituent(s), and drug-exposed cells with modified/perturbed cellular constituent(s).

Labeled cDNA is prepared from mRNA by oligo dT-primed or random-primed reverse transcription, both of which are well known in the art (see e.g., Klug and Berger, 1987, *Methods Enzymol.* 152:316–325). Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, *Nature Biotech.* 14:1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent label is used. For example, a radioactive label, or a pair of radioactive labels with distinct emission spectra, can be used (see Zhao et al., 1995, High density cDNA filter analysis: a novel approach for large-scale, quantitative analysis of gene expression, *Gene* 156:207; Pietu et al., 1996, Novel gene transcripts preferentially expressed in human muscles revealed by quantitative hybridization of a high density cDNA array, *Genome Res.* 6:492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, dATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™ II, LTI Inc.) at 42° C. for 60 min.

Hybridization to Microarrays

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York, which is incorporated in its entirety for all purposes. When the cDNA microarrays of Schena et al. are used, typical hybridization conditions are hybridization in 5 X SSC plus 0.2% SDS at 65° C. for 4 hours followed by washes at 25° C. in low stringency wash buffer (1 X SSC plus 0.2% SDS) followed by 10 minutes at 25° C. in high stringency wash buffer (0.1 X SSC plus 0.2% SDS) (Shena et al., 1996, *Proc. Natl. Acad. Sci. USA,* 93:10614). Useful hybridization conditions are also provided in, e.g., Tijessen, 1993, *Hybridization With Nucleic Acid Probes,* Elsevier Science Publishers B. V. and Kricka, 1992, Nonisotopic DNA Probe Techniques, Academic Press San Diego, Calif.

Signal Detection and Data Analysis

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, A DNA microarray system for analyzing complex DNA samples using two-color fluorescent probe hybridization, *Genome Research* 6:639–645, which is incorporated by reference in its entirety for all purposes). In a preferred embodiment, the arrays are scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6:639–645 and in other references cited herein. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores is preferably calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 3-fold to about 5-fold, but more sensitive methods are expected to be developed.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art. The magnitude of the relative perturbation is most preferably represented according to Equation 2 of Section 5.2.

Methods of Experimental Measurement

In one embodiment of the invention, transcript arrays reflecting the transcriptional state of a cell of interest are made by hybridizing a mixture of two differently labeled probes each corresponding (i.e., complementary) to the mRNA of a different cell of interest, to the microarray. According to the present invention, the two cells are of the same type, i.e., of the same species and strain, but may differ genetically at a small number (e.g., one, two, three, or five, preferably one) of loci. Alternatively, they are isogeneic and differ in their environmental history (e.g., exposed to a drug versus not exposed).

In order to perform experiments according to this invention, cells (of the biological system of interest) are prepared or grown in the presence of a first state of the cellular constituents input to the network model and also in the presence of a second state of these input cellular constituents. These states are determined by the experiments chosen to test the model. Typically, these states include modification/perturbation to certain of the input cellular constituents (such as by gene deletion) as well as exposure to one or more drugs. cDNAs (or mRNAs) are derived from the two cells and differently labeled according to the cell of origin, and are used to construct transcript arrays, which are measured to find the mRNAs with modified expression and the degree of modification due to exposure to the drug. Thereby, the response of the cell to this experiment is obtained, and is used in the methods of Section 5.2 and 5.2 to find an overall goodness of fit, and it statistical significance, of the network model to the cell.

In certain embodiments of this invention, it is advantageous to make measurements of graded drug exposure and of graded levels of the modification/perturbation control parameters. This is advantageous in the case of the continuous interpretation of the logical operators of the network model previously described in Section 5.1. It is also advantageous where graded exposures and modifications are used to clearly identify saturating levels. In this case, the density of levels of the graded drug exposure and graded perturbation control parameter is governed by the sharpness and structure in the individual gene responses—the steeper the steepest part of the response, the denser the levels needed to properly resolve the response. Preferably, six to ten levels of perturbation or exposure over a hundred-fold total range was just sufficient to resolve the gene expression responses. However, more exposures are preferably to more finely represent this pathway.

Further, it is preferable in order to reduce experimental error to reverse the fluorescent labels in two-color differential hybridization experiments to reduce biases peculiar to individual genes or array spot locations. In other words, it is preferable to first measure gene expression with one labeling (e.g., labeling cells exposed to the first input state with a first fluorochrome and cells exposed to the second input state with a second fluorochrome) of the mRNA from the two cells being measured, and then to measure gene expression from the two cells with reversed labeling (e.g., labeling cells exposed to the first input state with the second fluorochrome and cells exposed to the second input state with the first fluorochrome).

Multiple measurements of these input states provides additional indication and control of experimental error. Further, in the case of graded modifications/perturbations, multiple measurements over exposure levels and modification/perturbation control parameter levels provide additional experimental error control.

Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent 0 534858 A1, filed Sep. 24, 1992, by Zabeau et al.), or methods selecting restriction fragments with sites closest to a defined mRNA end (see, e.g., Prashar et al., 1996, Proc. Natl. Acad. Sci. USA 93:659–663). Other methods statistically sample cDNA pools, such as by sequencing sufficient bases (e.g., 20–50 bases) in each of multiple cDNAs to identify each cDNA, or by sequencing short tags (e.g., 9–10 bases) which are generated at known positions relative to a defined mRNA end (see, e.g., Velculescu, 1995, Science 270:484–487). pathway pattern.

5.5.2.2. MEASUREMENT OF OTHER ASPECTS

In various embodiments of the present invention, aspects of the biological state other than the transcriptional state, such as the translational state, the activity state, or mixed aspects can be measured in order to obtain drug and pathway responses. Details of these embodiments are described in this section.

Embodiments Based on Translational State Measurements

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to testing or confirming a biological network model of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array. and their binding is assayed with assays known in the art.

Alternatively, proteins can be separated by two-dimensional gel electrophoresis systems Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Nat'l Acad. Sci. USA* 93:1440–1445; Sagliocco et al., 1996, *Yeast* 12:1519–1533; Lander, 1996, *Science* 274:536–539. The resulting electropherograms can be analyzed by numerous techniques, including mass spectrometric techniques, western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or overexpression of a specific gene.

Embodiments Based on Other Aspects of the Biological State

Although monitoring cellular constituents other than mRNA abundances currently presents certain technical difficulties not encountered in monitoring mRNAs, it will be apparent to those of skill in the art that the use of methods of this invention, including application of various known methods of modifying/perturbing cellular constituents input to a network model, are applicable to any cellular constituent that can be monitored.

In particular, where activities of proteins relevant to the characterization of drug action can be measured, embodiments of this invention can be based on such measurements. Activity measurements can be performed by any functional, biochemical, or physical means appropriate to the particular activity being characterized. Where the activity involves a chemical transformation, the cellular protein can be contacted with the natural substrates, and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.6. COMPUTER IMPLEMENTATIONS

Figure 11:
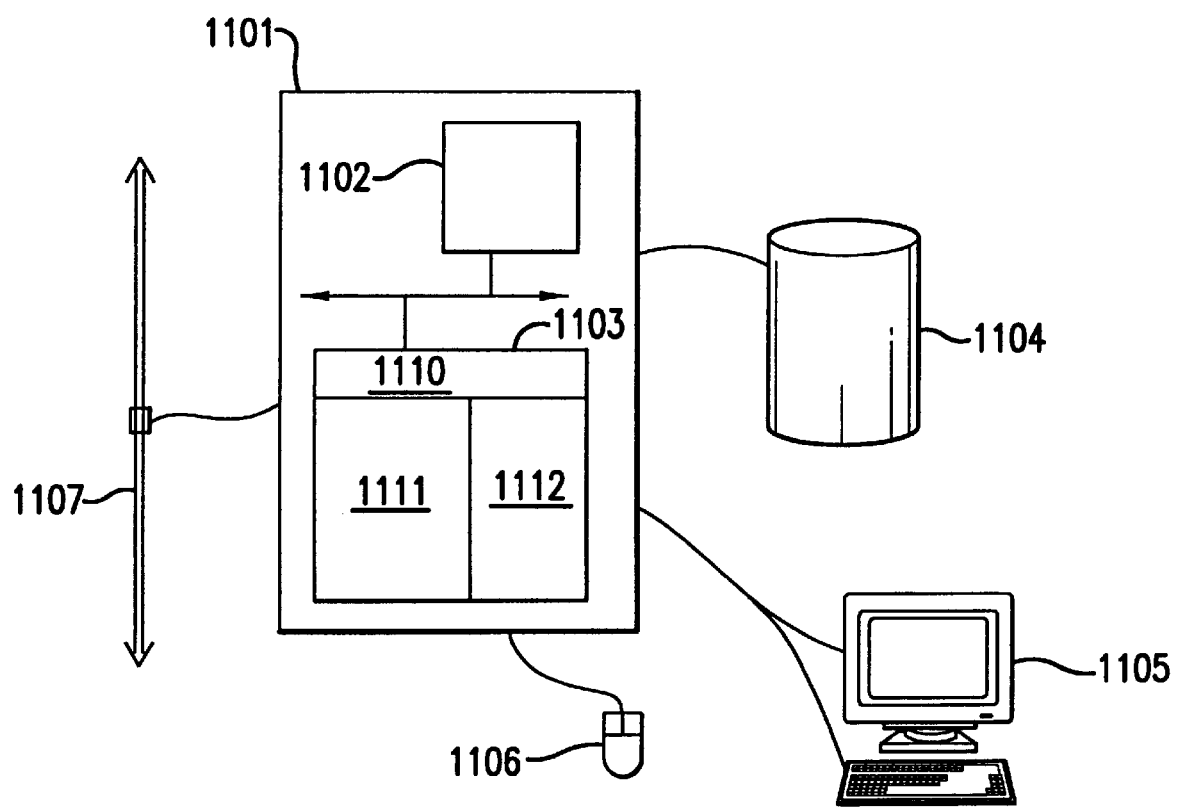
FIG. 11 illustrates an exemplary embodiment of a computer system of this invention wherein the components are all housed within a single hardware platform.

In a preferred embodiment, the computation steps of the previous methods are implemented on a computer system or on one or more networked computer systems in order to provide a powerful and convenient facility for forming and testing network models of biological systems. FIG. 11 illustrates an exemplary computer system suitable for implementation of the analytic methods of this invention. Computer system 1101 is illustrated as a single hardware platform comprising internal components and being linked to external components. The internal components of this computer system include processor element 1102 interconnected with main memory 1103. For example computer system 1101 can be an Intel Pentium based processor of 200 Mhz or greater clock rate and with 32 MB or more of main memory.

The external components include mass storage 1104. This mass storage can be one or more hard disks (which are typically packaged together with the processor and memory). Typically, such hard disks provide for at least 1 GB of storage. Other external components include user interface device 105, which can be a monitor and keyboards, together with pointing device 1106, which can be a "mouse", or other graphic input devices (not illustrated). Typically, computer system 1101 is also linked to other local computer systems, remote computer systems, or wide area communication networks, such as the Internet. This network link allows computer system 1101 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 1104. Alternatively, the software components may be stored on removable media such as floppy disks or CD-ROM (not illustrated). Software component 1110 represents the operating system, which is responsible for managing computer system 1101 and its network interconnections. This operating system can be, e.g., of the Microsoft Windows family, such as Windows 95, Windows 98, or Windows NT, or a Unix operating system, such as Sun Solaris. Software component 1111 represents common languages and functions conveniently present on this system to assist programs implementing the methods specific to this invention. Languages that can be used to program the analytic methods of this invention include C, C++, or, less preferably, JAVA. Most preferably, the methods of this invention are programmed in mathematical software packages which allow symbolic entry of equations and high-level specification of processing, including algorithms to be used, thereby freeing a user of the need to procedurally program individual equations or algorithms. Such packages include, e.g., Matlab from Mathworks (Natick, Mass.), Mathematica from Wolfram Research (Champaign, Ill.), and MathCAD from Mathsoft (Cambridge, Mass.). Software component 1112 represents the analytical methods of the invention as programmed in a procedural language or symbolic package.

Figure 12:
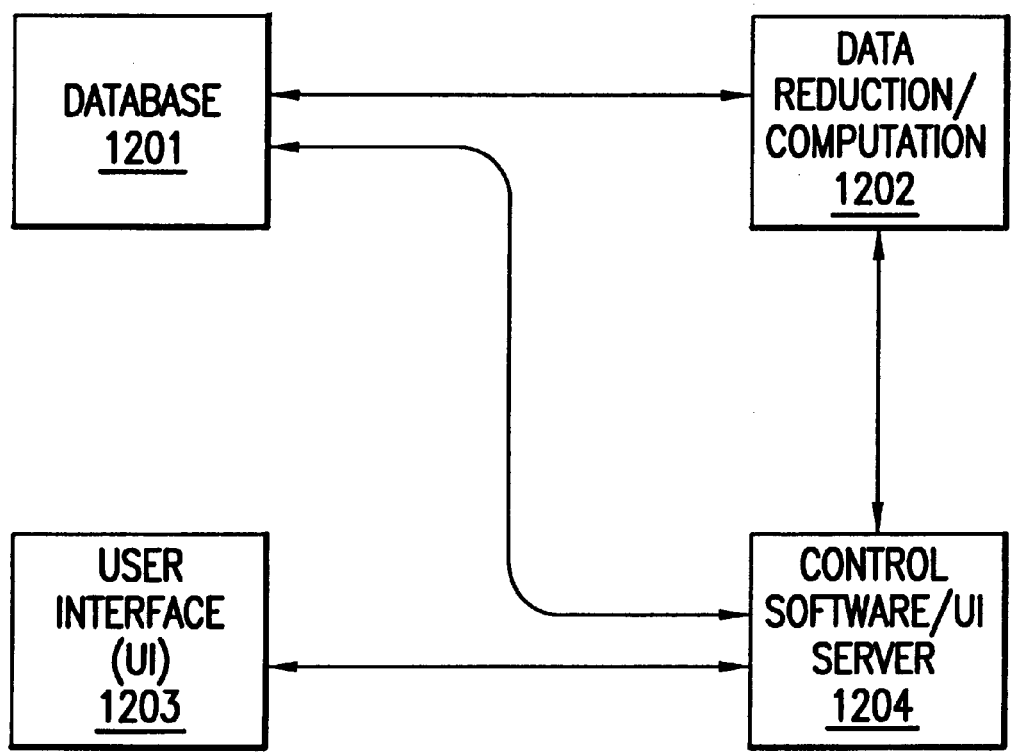
FIG. 12 illustrates generally a preferred embodiment of the analytic software components of the computer system of this invention.

In preferred embodiments, the analytic software component actually comprises four separate software components which interact with each other as illustrated in FIG. 12. Analytic software component 1201 represents a database containing all data necessary for the operation of the system.

Such data will generally include, but is not necessarily limited to, results of prior experiments, genome data, experimental procedures and cost, and other information which will be apparent to those skilled in the art. Analytic software component 1202 represents a data reduction and computation component comprising one or more programs which execute the analytic methods of the invention, including: the methods for testing a network model, described in Section 5.2; the methods for determining the statistical significance of a network model, described in Section 5.3; and the methods for the choice of efficient experiments, described in Section 5.4. Analytic software component 1203 represents a user interface (UI) which provides a user of the computer system with control and input of test network models, and, optionally, experimental data. The user interface may comprise a drag-and-drop interface for specifying hypotheses to the system. The user interface may also comprise means for loading network models and/or experimental data from the mass storage component (e.g., the hard drive), from removable media (e.g., floppy disks or CD-ROM), or from a different computer system communicating with the instant system over a network (e.g., a local area network, or a wide area communication network such as the internet). Analytic software component 1204 represents the control software, also referred to herein as a UI sever, which controls the other software components of the computer system.

Figure 13:
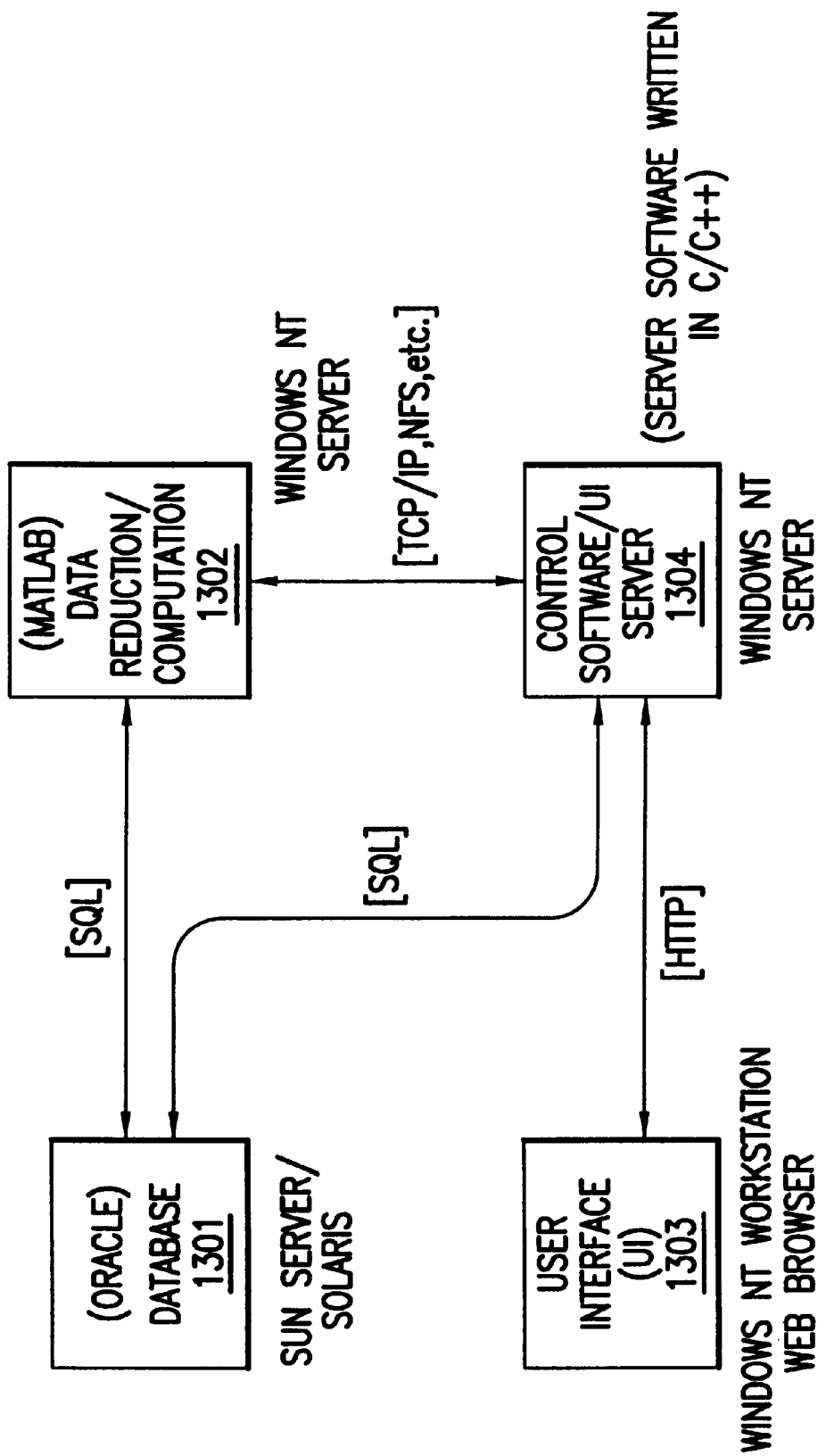
FIG. 13 illustrates a exemplary embodiment of the computer system of the invention wherein the analytic software components are housed on separate hardware platforms.

In another preferred embodiment, the computer system of the invention comprises a plurality of hardware platforms, each having the hardware components described above for FIG. 11 (i.e., memory, processors, etc.). In such an embodiment, one or more of the analytic software components described above may be located on different hardware platforms of the system. An exemplary implementation of this embodiment is illustrated in FIG. 13. In FIG. 13, the UI component is operating from a remote Web Browser (e.g., Netscape Navigator or Microsoft Internet Explorer) running on a Microsoft Windows NT workstation (1303). The Control Software component operates on an HTTP server (1304) which operates in conjunction with specialized software written in C/C++ and/or Java. The database component in this example comprises an Oracle database operating on a Sun Server (1301) which employs the Sun Solaris operating system. The data analysis takes place within Matlab (from Mathworks, Natick, Mass.), running on a Windows NT Server (1302), in conjunction with specialized Matlab programs which implement the data analysis and correlation methods of this invention.

The components 1302 and 1304 communicate with each other over a network, such as the internet, using TCP/IP based network procols. Communication to the database is SQL based, or a variant thereof. The Control module (1304) communicates with the Data Reduction module (1302) via TCP/IP, file sharing via NFS, etc. The Control software communicates with the user interface (1303) via HTTP and downloads specialized Java code to it.

Alternative systems and methods for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

Figure 10:
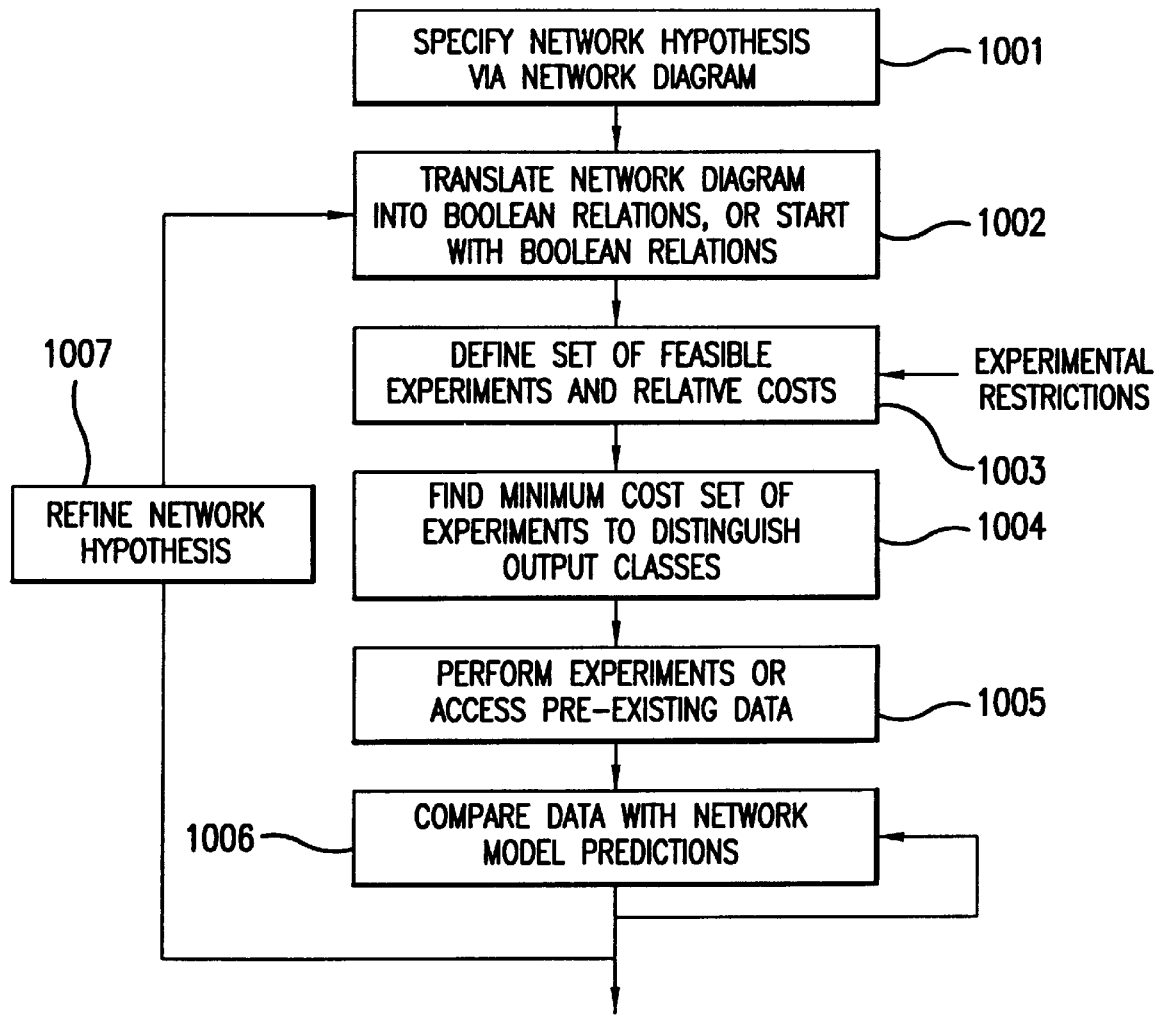
FIG. 10 illustrates an implementation of the methods of this invention.

In an exemplary implementation, to practice the methods of this invention, the previously described computer system implements the detailed process illustrated in FIG. 10. In step 1001, an initial network model is specified by a user, preferably by means of graphical user interface accessed with pointing device 1106. This interface can be programmed to provide a drag-and-drop metaphor, allowing the user to assemble a network model by manipulating graphical icons representing network components on the computer screen. FIGS. 2B, 3B, 4B, and 5B illustrate possible graphical presentations of network models. This interface can be programmed in using any of the conventional and available graphical user interface APIs (application programming interfaces). For instance, implementation might be done in Java's Abstract Windowing Toolkit, Tcl/Tk, Win32 with out without Microsoft Foundation Classes, the Macintosh user interface, or for the X-Windows system using an appropriate widget toolkit such as Motif or the Open Look Intrinsics Toolkit (OLIT) and Xt toolkit for user interface widget creation.

In step 1002, implementing programs translate the graphical network model into logical relations between cellular constituents input to the network model and output classes that are equivalent to the graphical representation. A convenient intermediate representation is Boolean relations as illustrated and exemplified previously. Alternatively, the logical relations defining the network model can be directly input. Such translation from schematic layout to Boolean relations may proceed in several steps: labeling of external nodes, labeling of internal nodes, and recording of the specific logical operator between all connected nodes. The data structures thus constructed may in fact, be generated at the time the user graphically lays down the circuit description, and stored in the computers memory and file system. Moreover, visual circuit design programs are readily available from third party suppliers of software, whose tools we may make use of in the process of describing biological networks. Such tools, for example Synario (MINC Inc., Colorado Springs, Colo.), will produce computer-industry standard descriptions of logic gate networks in various standard formats such as the network lists of SPICE, or the more exhaustive VHDL, Verilog, Abel, and Altera hardware description languages. The software would use the output of such tools or the output of a graphical modeler to render the necessary Boolean relations to be fed into steps 1003 and 1004 of the process.

In step 1003, feasible experiments are defined. First, feasible experiments are specified through constraints which limit the modifications of perturbations to the input cellular constituents that are experimentally possible. For example, such constraints can include that deletions of only a single gene at one time are allowed, or that exposure to only a single drug is allowed. Second, costs are assigned to the feasible experimental conditions. For example, the costs of rate and expensive drugs or of the effort in performing gene deletions can be considered in assigning these costs. These costs are used to weight the various choices considered during the course of choosing the optimal set of experiments to distinguish the desired network output classes.

In step 1004, an efficient and complete set of experiments is derived according to the methods of Section 5.4, and the details presented above. These experiments are feasible, since they satisfy the constraints input in step 1003. They are complete in that they can distinguish all output classes. Finally, they are efficient in that they minimize an objective function based on the costs input previously.

In step 1005, the chosen experiments are performed in the laboratory to obtain the measurement data, which is input to computer storage. This data is typically stored in mass storage or mass storage on other network attached computer systems) is assembled. Alternatively, the data may be stored on removable media such as floppy disks or CD-ROM.

Finally, in step 1006, the methods described in Sections 5.2 and 5.3 are carried out to obtain both an overall goodness of fit of the network model to the experimental data input in step 1005, as well as the statistical significance of the overall goodness of fit. The methods may be implemented as a series of functions in a commercially available software package such as Matlab (from Mathworks, Natick, Mass.) or S-Plus from Mathsoft (Cambridge, Mass.) for statistical analysis. Alternatively, various procedures on the critical path may be written in a programming language such as C/C++. The control and server software may also bee custom written for in a language such as C/C++ or Java.

The system, as implemented in components described above with reference to FIGS. 12 and 13, is designed such that each component may operate in an independent, modular and scalable manner. Each component may operate on the same or on different hardware from other components. Such design allows the system to scale up as the size and complexity of the problems to be solved increases and as new hardware and software becomes available.

The results determined in step 1006 are output to the user in a convenient, preferably graphical, format and may also be stored for future reference in mass storage, such as a hard drive, or on removable media such as floppy disks or CD-ROM. At least the overall goodness of fit and its significance are output. Preferably the output classes that best fit user selected cellular constituents are also output. Further, data from any intermediate computational steps can optionally be stored and output. For example, the empirically determined histogram of goodness of fit values can preferably be displayed on user request.

Optionally, the original network model can be refined in step 1007 in view of previous results in order to obtain a further network model, which in turn may be tested and confirmed according to the previous steps 1002 through 1006. If the further network model is found to have a higher significance that the original network model, it can be accepted as a refined and improved model. This process can be repeated to obtain increasingly refined and improved models as described in Sections 5.1 and 5.2.

6. EXAMPLE

The following example is presented by way of illustration of the previously described invention and is not limiting of that description.

Figure 7A:
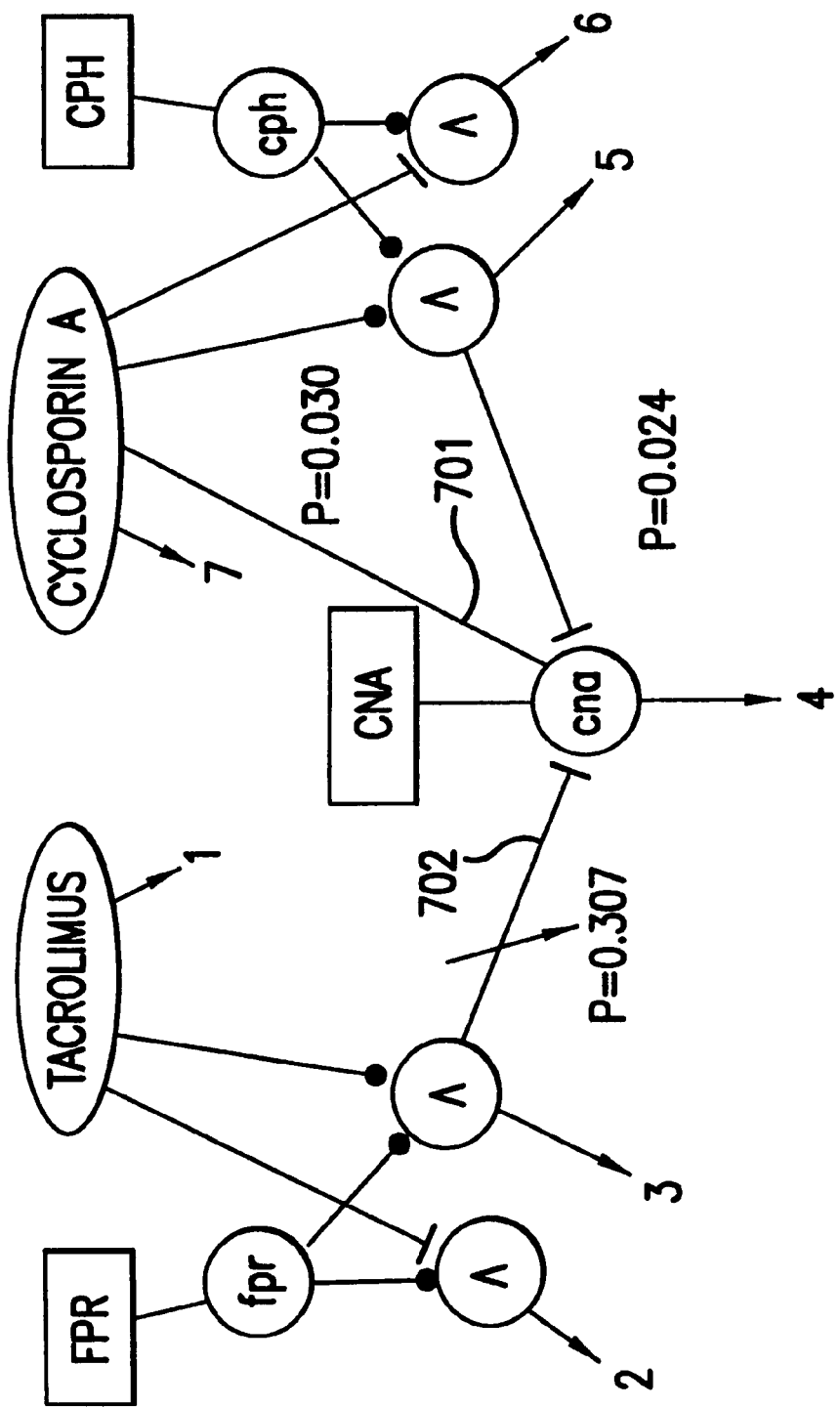
FIG. 7A illustrates an exemplary network model relevant to the immunosuppressant drugs FK506 and Cyclosporin A.

FIG. 7A illustrates a biological network model, relevant to immunosuppression, that was fit to observations and measurements in yeast cells. The input cellular constituents of this network model are two immunosuppressive drugs, FK506 (also known as tacrolimus) and cyclosporin A (called herein CyA), and the proteins (or encoding genes) fpr (a FK506 binding protein), cna (the calcineurin protein ), and cph (a CyA binding protein). The output classes are labeled 1, 2, 3, 4, 5, 6, and 7. FIG. 7A presents the logical structure of the operator (the node labeled cna being an AND operator). The P-values of network significance are explained subsequently.

In mammals, FK506 and CyA are known to act to inhibit the function of cna through separate but convergent pathways of a structure similar to that of the network model. The cna protein is necessary to allow nuclear translocation of the nuclear factor for activating T-cells (NF-AT), and inhibiting calcineurin prevents proliferation of T-cells in response to antigen, suppressing the immune response. The intermediate fpr and cph proteins are immunophilins which are proline isomerases whose normal function includes correct protein folding. The drugs make complexes with their respective binding proteins that are inhibitory to cna, and also fail to perform the native protein folding function.

In yeast, from which data was obtained, similar pathways exist with homologous proteins. However, the cna homologue is necessary for recovery from factor mating arrest.

FIG. 7B illustrates the unnormalized influence matrix which was derived from the network model of FIG. 7A. This influence matrix presumes that the direction of change of cellular constituents can be determined from the subsequent experiments. The feasible experiments were limited to those in which cells with single gene deletions were compared to wild-type cells (herein referred to a "WT"), in which cells exposed to FK506 or CyA were compared with cells not so exposed, and in which comparisons of drug exposure were done in cells with single gene deletions.

There were 12 experimental pairs of such feasible experiments that are naturally relevant to this network model. These experiments are set out on the heading of the influence matrix. The seven rows of the influence matrix correspond to the seven output classes defined by this network hypothesis.

In detail, for example, the "WT vs. WT" experiment was a control experiment where both perturbed and unperturbed states were the same wild type strain, and in which, accordingly, no changes in any cellular constituent were expected to be observed. The other experiments are labeled appropriately. For example, the experiment labeled "±FK506 (−cna)" refers to a comparison between cells with the cna gene deleted and exposed to FK506 and cells with the cna gene deleted but not exposed to FK506. This particular experiment caused no changes in output class 4 (the class representing effects of cna), because the cna protein has been eliminated. Hence there is a "0" row 4 of this column. Exposure to FK506 (tacrolimus) affected output classes 1, 2, and 3, all of which are influenced by FK506. Comparing a cell exposed to FK506 with a cell not so exposed, output class 1 experienced a loss of the drug effect; hence the "−1" entry in the unnormalized influence matrix. Output class 2 experienced a loss of drug inhibition on the fpr protein; hence a "1" entry. Output class 3 experienced a loss of the effects of drug-protein complex; hence a "−1" entry.

Data used to test the network model of FIG. 7A consisted of the 12 experiment involving the pairs of comparisons listed in the heading of the matrix FIG. 7B. These data were obtained from two-color fluorescent hybridizations of the yeast *Saccharomyces cerevisiae* cDNA samples to cDNA transcript arrays containing all the 6249 expressed genes of the yeast genome, according to the methods of Section 5.5.2. For each pair of experimental comparisons, the data collected consisted of the pairs of the expression levels for each of the 6249 genes. From this genome wide expression data, a subset of 140 expressed genes were selected which exceeded the threshold of having changes greater than a factor of two in at least two of the 12 experiments. The two abundance measurements for each of these 140 selected genes in each experiment were used to generate the measure of change, x, according to Section 5.2. The over-all goodness of fit was computed, also according to Section 5.2, which involved normalizing the unnormalized influence matrix of FIG. 7B and finding the best fitting output class from among the seven output classes for each of the 140 selected genes. The goodness of fit of the network model of FIG. 7A (the sum of the individual goodness of fit values for the 140 selected genes) to the yeast expression data was found to be 360.

The statistical significance of this goodness of fit was tested according to the methods of Section 5.3. For each of the 140 selected genes, the 12 values of x arising from the 12 experiments were randomly permuted in order. Thereby, the correspondence between the model and the data was randomized. This randomization was performed independently for each gene. For each such data randomization and for each gene, the best fitting output classes were redetermined and the over-all goodness of fit redetermined for each data randomization. These randomizations and redeterminations were repeated 1000 times and the resulting goodness of fit values plotted as a histogram.

Figure 8:
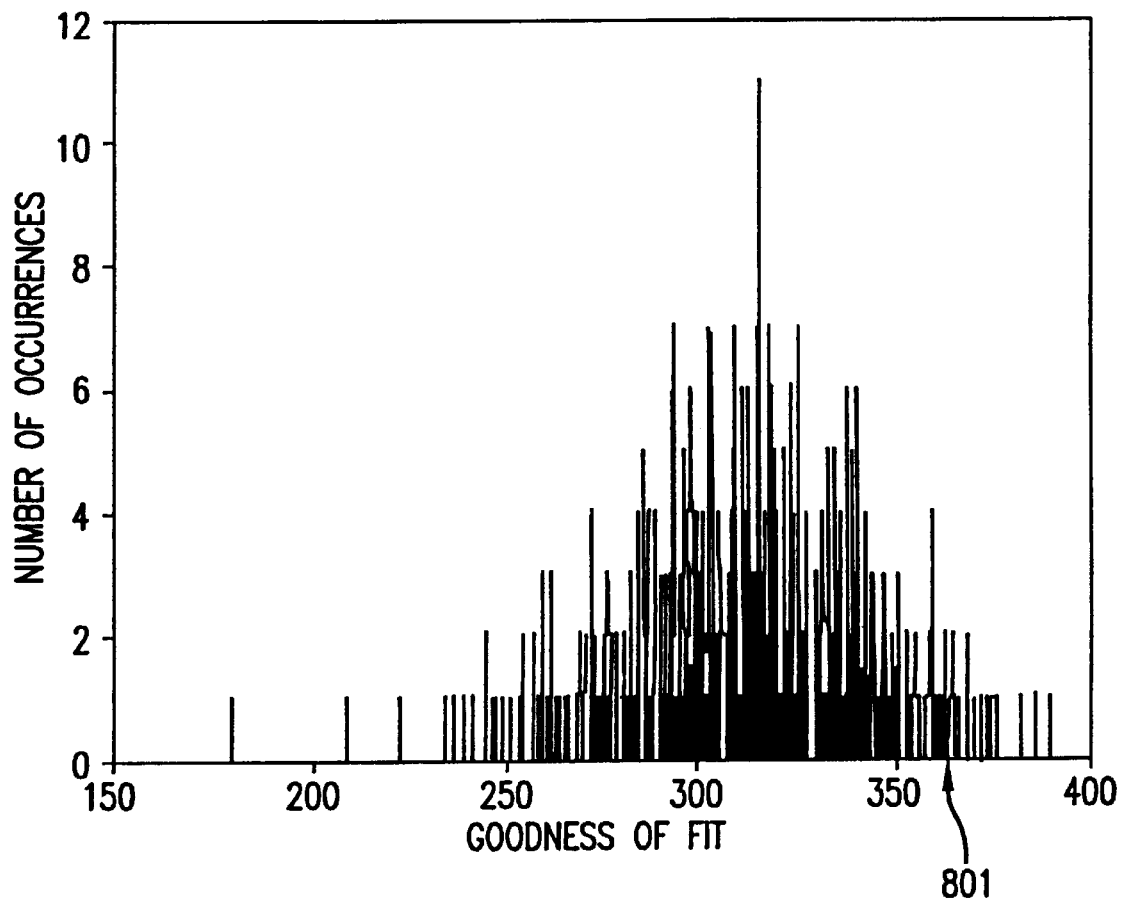
FIG. 8 illustrates a histogram of goodness of fit determined according to the methods of this invention.

FIG. 8 illustrates the resulting histogram. The horizontal axis plots the goodness fit values, and the vertical axis plots the number of time each goodness of fit value was found in the 1000 randomizations. This histogram was, accordingly, the probability distribution of the goodness of fit values under the null hypothesis that the network model had no relation to the observed data. The position of the goodness of fit actually found, 360, indicated by arrow 801, with respect to this distribution was then probability of this null hypothesis. Since 2.4% of the random goodness of fit values were greater that the goodness of fit actually found, the P-value is 0.024. Therefore, it was concluded that the network model of FIG. 7A is significantly correlated with the behavior of yeast.

Several alternative network models were tested in order to search for a refined model. In a first alternative network model, link 701 from CyA to the cna protein was added. An overall goodness of fit value was determined for this first alternative as described above. The P-value determined was 0.030. This indicated that the original network model and the first alternative network model were substantially equally significant.

In a second alternative network model, link 702 from the fpr protein to the cna protein was made, and an overall goodness of fit value was determined for this second alternative as described above. The P-value determined was 0.307. This indicated that the second alternative network model had substantially no significance in explaining the yeast data, and was therefore not an improvement over the prior network model.

The comparisons of these alternative network models with the original network model illustrates that use of the P-values allows correct choice between alternative network models.

Further, individual ones of the selected 140 genes were assigned to best fitting output classes as described in Section 5.2. There are 7 classes shown in FIGS. 7A–B. For example, output classes 2 and 3 could be considered "side effects" or "off-target" effects of FK506, output class 4 being the desired "primary" or "target" effect of FK506. The best fitting methods of Section 5.2 were applied to this data, and showed that output class 4 was a significant best fitting class of many genes known to be regulated in a calcineurin-dependent way.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for testing or confirming a network model for a biological system,
    said network model comprising:
        a plurality of input constituents; and
        a plurality of output classes represented by boolean functions of values of perturbations or modifications to one or more of said input constituents;
    said method comprising:
        (a) assigning one or more cellular constituents to a particular output class having a defined change that best matches a measured change, wherein
            (i) said measured change is provided by data from one or more network testing experiments, said data comprising measured changes in the one or more cellular constituents from a first input state to a second input state,
            (ii) said defined change is provided by an influence matrix which defines changes of each output class from the first input state to the second input state according to the network model; and
        (b) determining an overall goodness of fit of said data to the network model, wherein the network model is tested or confirmed by said overall goodness of fit.

2. The method of claim 1 wherein, for each of the one or more cellular constituents assigned to a particular output class, the particular output class having a defined change that best matches a measured change is identified by means of an objective measure of the difference between said measured change and said defined change.

3. The method of claim 2 wherein
    the objective measure of the difference between said measured change and said defined change for each of the one or more cellular constituents assigned to a particular output class comprises the maximum likelihood of observing said measured change of said cellular constituent.

4. The method of claim 3 wherein said overall goodness of fit comprises the product of said maximum likelihoods for each of the one or more cellular constituents.

5. The method of claim 2 wherein said objective measure comprises a correlation of said measured change of said cellular constituent with said defined change of said cellular constituent for one of said output classes.

6. The method of claim 5 wherein said objective measure comprises the absolute value of said correlation.

7. The method of claim 5 wherein said correlation is provided by a method comprising correlating the absolute values of said measured change of said cellular constituent with said defined change of said cellular constituent for one of said output class.

8. The method of claim 1 wherein said step of determining an overall goodness of fit of said data to the network model comprises:
    (i) determining, for each of the one or more cellular constituents assigned to a particular output class, a value of an objective measure of the difference between the measured change and the defined change; and
    (ii) combining the values of said objective measure for each of the one or more cellular constituents assigned to a particular output class,
    wherein said combined values of said objective measure comprise said overall goodness of fit.

9. The method of claim 8 wherein the values of said objective measure for each of the one or more cellular constituents assigned to a particular output class are additively combined.

10. The method of claim 8 further comprising a step of assessing the significance of said overall goodness of fit by a method comprising
   (i) obtaining an expected probability distribution of overall goodness of fit values, and
   (ii) assessing the statistical significance of said overall goodness of fit in view of said expected probability distribution.

11. The method of claim 10 wherein said expected probability distribution is obtained by a method comprising repeatedly:
   (i) randomly permuting the measured changes for each of the one or more cellular constituents with respect to the one or more network testing experiments, to produce randomly permuted measured changes; and
   (ii) determining an overall goodness of fit value for said randomly permuted measured changes; until a plurality of overall goodness of fit values is generated,
   wherein said plurality of overall goodness of fit values comprises said expected probability distribution of overall goodness of fit values.

12. The method of claim 1 further wherein said network testing experiments are chosen according to a method comprising:
   (a) identifying a covering set of input states, said covering set of input states comprising, for any pair of output classes, input states which distinguish said pair of output classes; and
   (b) choosing pairs of input states, each pair of input states comprising
      (i) a first input state in said covering set, and
      (ii) a second input state in said covering set,
      wherein, for any pair of output classes, said first input state and said second input state distinguish said pair of output classes,
   wherein said chosen network testing experiments comprise measured changes in one or more cellular constituents from the first input state to the second input state of each chosen pair of input states.

13. The method of claim 12 wherein said step of identifying a covering set of input states comprises determining a solution to a linear integer programming problem, wherein
   said linear integer programming problem comprises a pair of inequalities for each output class, said pair of inequalities consisting of:
      (i) a first inequality representing all input states in which output classes in a pair of output classes have different behaviors, and
      (ii) a second inequality representing all input states in which output classes in a pair of output classes have the same behavior.

14. The method of claim 13
   wherein all input states in said covering set of input states are assigned individual experimental costs, and
   wherein the solution to said linear integer programming problem minimizes the sum of individual experimental costs of all input states in said covering set of input states.

15. The method of claim 13 wherein the solution to said linear integer programming problem is determined by means of a branch-and-bound algorithm.

16. The method of claim 12 wherein said step of choosing pairs of input states comprises determining a solution to a linear integer programming problem, wherein
   said linear integer programming problem comprises an inequality for each possible pair of output classes, said inequality representing all pairs of input states in the covering set in which output classes in said pair of output classes have different behaviors.

17. The method of claim 16 wherein the solution to said linear integer programming problem is determined by means of a branch-and-bound algorithm.

18. The method of claim 1
   wherein said cellular constituents comprise protein species present in said biological system; and
   wherein said measured changes in the one or more cellular constituents comprise measured changes in activities of said protein species.

19. The method of claim 1 wherein said perturbations or modifications to one or more input constituents is done by a method comprising modifying said one or more input constituents.

20. The method of claim 19 wherein said one or more input constituents are modified by a method comprising deleting genes encoding said input constituents.

21. The method of claim 19 wherein said one or more input constituents are modified by a method comprising causing expression of said one or more input constituents under the control of a controllable expression system.

22. The method of claim 19 wherein said one or more input constituents are modified by a method comprising controllable transfection of genes expressing said one or more input constituents.

23. The method of claim 19 wherein said one or more input constituents are modified by a method comprising controllably decreasing abundances of RNA species encoding said one or more input constituents in said biological system.

24. The method of claim 23 wherein said method of controllably decreasing said abundances of RNA species comprises exposing said biological system to ribozymes targeted to cleave said RNA species.

25. The method of claim 19 wherein said one or more input constituents are modified by a method comprising controllably decreasing the rate of translation of RNA species encoding said one or more input constituents in said biological system.

26. The method of claim 25 wherein said method of controllably decreasing the rate of translation of RNA species comprises exposing said biological system to antisense nucleic acids or antisense nucleic acid mimics that hybridize to said RNA species or to DNA encoding said RNA species.

27. The method of claim 19 wherein said one or more input cellular constituents are abundances of protein species or activities of protein species, and wherein said one or more input constituents are modified by a method comprising controllably decreasing one or more of said abundances in said biological system.

28. The method of claim 27 wherein said method of controllably decreasing one or more of said abundances comprises causing expression in said biological system of one or more of said protein species as fusion proteins comprising said protein species and a degron, wherein said degron is controllable to increase the rate of degradation of said protein species.

29. The method of claim 19 wherein said one or more input constituents are activities of protein species, and wherein said one or more input constituents are modified by a method comprising controllably decreasing said activities in said biological system.

30. The method of claim 29 wherein said method of controllably decreasing said activities comprises exposing said biological system to antibodies, wherein said antibodies bind said protein species.

31. The method of claim 29 wherein said method of controllably decreasing said activities comprises exposing said biological system to drugs which directly and specifically inhibit said activities of said protein species.

32. The method of claim 29 wherein said method of controllably decreasing said activities comprises exposing said biological system to a dominant negative mutant protein species, wherein said dominant negative mutant protein species are proteins inhibiting said activities.

33. The method of claim 1
wherein said cellular constituents comprise protein species present in said biological system; and
wherein said measured changes in the one or more cellular constituents comprise measured changes in abundances of said protein species.

34. The method of claim 33 wherein the abundances of said plurality of protein species are measured by a method comprising contacting an antibody array with proteins from said biological system, wherein said antibody array comprises a surface with attached antibodies, said antibodies capable of binding with said plurality of protein species.

35. The method of claim 33 wherein the abundances of said plurality of protein species are measured by a method comprising performing two-dimensional electrophoresis of proteins from said biological system.

36. The method of claim 1 further comprising a step of assessing the statistical signifcance of alternative network models according to the Maximum Likelihood method.

37. The method of claim 1 wherein said changes defined by said influence matrix comprise:
(i) indications of no change of a cellular constituent from the first input state to the second input state, and
(ii) indications of change of a cellular constituent from the first input state to the second input state.

38. The method of claim 1 wherein said changes defined by said normalized influence matrix comprise:
(i) indications of no change of a cellular constituent from the first input state to the second input state, and
(ii) indications of change of a cellular constituent from the first input state to the second input state and the direction of said change of the cellular constituent from the first input state to the second input state.

39. The method of claim 1 wherein said changes defined by said normalized influence matrix comprise:
(i) indications of no change of a cellular constituent from the first input state to the second input state,
(ii) indications of relative increase of a cellular constituent from the first input state to the second input state, and
(iii) indications of relative decrease of a cellular constituent from the first input state to the second input state.

40. The method of claim 1 wherein said influence matrix is normalized such that:
(i) the mean value of all elements of said influence matrix defining the behavior of an output class is zero, and
(ii) the sum of the squares of all elements of said influence matrix defining the behavior of an output class has the same value as the sum of the squares of all elements of said influence matrix defining the behavior of any other output class.

41. The method of claim 1 wherein said measured change is normalized by expected additive and multiplicative measurement errors.

42. The method of claim 1 wherein said biological system comprises one or more cells of a yeast.

43. The method of claim 42 wherein said yeast is a strain of *Saccharomyces cerevisiae*.

44. The method of claim 1 wherein at least one of said input constituents comprises one or more drugs.

45. The method of claim 1
wherein said cellular constituents comprise RNA species present in said biological system;and
wherein said measured changes in the one or more cellular constituents comprise measured changes in abundances of said RNA species.

46. The method of claim 45 wherein the abundances of said plurality of RNA species are measured by a method comprising contacting a gene transcript array with RNA from said biological system, or with cDNA derived therefrom, wherein a gene transcript array comprises a surface with attached nucleic acids or nucleic acid mimics, said nucleic acids or nucleic acid mimics capable of hybridizing with said plurality of RNA species, or with cDNA derived therefrom.

47. The method of claim 46 wherein said measured changes in the one or more cellular constituents from a first input state to a second input state are provided by a method comprising:
(i) contacting one or more gene transcript arrays with RNA, or with cDNA derived therefrom, from said biological system in said first input state, and
(ii) contacting one or more gene transcript arra s with RNA, or with cDNA derived therefrom, from said biological system in said second input state.

48. A computer system for testing or confirming a network model for a biological system,
said network model comprising:
a plurality of input constituents; and
a plurality of output classes represented by boolean functions of values of perturbations or modifications to one or more of said input constituents,
said computer system comprising:
a processor;
a memory coupled to said processor and encoding one or more programs, said one or more programs causing said processor to execute steps of:
(a) assigning one or more cellular constituents to a particular output class having a defined change that best matches a measured change, wherein
(i) said measured change is provided by data from one or more network testing experiments, said data comprising measured changes in the one or more cellular constituents from a first input state to a second input state,
(ii) said defined change is provided by an influence matrix which defines changes of each output class from the first input state to the second input state according to the network model; and
(b) determining an overall goodness of fit of said data to the network model, wherein the network model is tested or confirmed by said overall goodness of fit.

49. The computer system of claim 48 wherein
said one or more programs further cause said processor to execute a step of determining a value of an objective measure of the difference between said measured change and said defined change; and said step of assigning said one or more cellular constituents to the particular output class is done according to said value of the objective measure.

50. The computer system of claim 48 wherein said one or more programs cause the processor to execute the step of determining an overall goodness of fit of said data to the network model by further executing steps comprising:
   (i) determining, for each of the one or more cellular constituents assigned to an output class, a value of an objective measure of the difference between the measured change and the defined change; and
   (ii) combining said values of said objective measure for each of the one or more cellular constituents assigned to an output class,
   wherein said combined values of said objective measure comprise said overall goodness of fit.

51. The computer system of claim 50 wherein said one or more programs further cause said processor to execute steps of:
   (i) obtaining an expected probability distribution of overall goodness of fit values; and
   (ii) determining a statistical significance of said overall goodness of fit from said expected probability distribution.

52. The computer system of claim 51 wherein said one or more programs cause said processor to execute the step of obtaining an expected probability distribution of overall goodness of fit values by further executing steps which comprise repeatedly:
   (i) randomly permuting the measured changes for each of the one or more cellular constituents with respect to the one or more network testing experiment so that randomly permuted measured changes are produced; and
   (ii) determining an overall goodness of fit value for said randomly permuted measured changes,
   until a plurality of overall goodness of fit values is generated, and
   wherein said plurality of overall goodness of fit values comprises said expected probability distribution of overall goodness of fit values.

53. A computer system for choosing one or more network testing experiments for testing or confirming a network model for a biological system,
   said network model comprising:
      a plurality of input constituents; and
      a plurality of output classes represented by boolean functions of values of perturbations or modifications to one or more of said input constituents,
   said computer system comprising:
      a processor; and
      a memory coupled to said processor and encoding one or more programs,
   said one or more programs causing said processor to execute steps of:
      (a) identifying a covering set of input states, said covering set of input states comprising, for any pair of output classes, input states which distinguish said pair of output classes; and
      (b) choosing pairs of input states, each pair of input states comprising
         (i) a first input state in said covering set, and
         (ii) a second input state in said covering set,
         wherein, for any pair of output classes, said first input state and said second input state distinguish said pair of output classes,
   wherein said chosen network testing experiments comprise measured changes in one or more cellular constituents from the first input state to the second input state of each chosen pair of input states.

54. A method for testing or confirming a network model for a biological system,
   said network model comprising:
      a plurality of input constituents; and
      a plurality of output classes represented by boolean functions of values of perturbations or modifications to one or more of said input constituents,
   said method comprising:
      (a) measuring changes of one or more cellular constituents in one or more network testing experiments, which network testing experiments comprise perturbations or modifications of one or more of said input constituents from a first input state to a second input state;
      (b) constructing an influence matrix that defines changes for each output class from said first input state to said second input state according to said network model;
      (c) assigning said one or more cellular constituents to one or more output classes for which the defined changes from the influence matrix best match the measured changes provided by step (a) of each of said one or more cellular constituents; and
      (d) determining an overall goodness of fit of said measured changes to the network model.

55. The method of claim 54 wherein said network testing experiments are chosen according to a method comprising:
   (i) identifying a covering set of input states, said covering set of input states comprising, for any pair of output classes, input states which distinguish said pair of output classes; and
   (ii) choosing pairs of input states, each pair of input states comprising
      a first input state in said covering set, and
      a second input state in said covering set,
   wherein, for any pair of output classes, said first input state and said second input state in said pairs of input states distinguish said pair of output classes, and
   wherein said chosen network testing experiments comprise perturbations or modifications of one or more cellular constituents from said first input state to said second input state in said pairs of input states.

56. The method of claim 55 wherein said step of identifying a covering set of input states comprises determining a solution to a linear integer programming problem, wherein said linear integer programming problem comprises a pair of inequalities for each output class, said pair of inequalities consisting of:
   (i) a first inequality representing all input states in which output classes in a pair of output classes have different behaviors, and
   (ii) a second inequality representing all input states in which output classes in a pair of output classes have the same behavior.

57. The method of claim 56 wherein the solution to said linear integer programming problem is determined by means of a branch-and-bound algorithm.

58. The method of claim 55 wherein said step of choosing pairs of input states comprises determining a solution to a linear integer programming problem, wherein said linear integer programming problem comprises an inequality for each possible pair of output classes, said inequality representing all pairs of input states in the covering set in which output classes in said pair of output classes have different behaviors.

59. The method of claim 58 wherein the solution to said linear integer programming problem is determined by means of a branch-and-bound algorithm.

60. A method of choosing one or more network testing experiments for testing or confirming a network model for a biological system, said network model comprising:
- a plurality of input constituents; and
- a plurality of output classes represented by boolean functions of values of perturbations or modifications to one or more of said input constituents, said method comprising:
- (a) identifying a covering set of input states, said covering set of input states comprising, for any pair of output classes, input states which distinguish said pair of output classes; and
- (b) choosing pairs of input states, each pair of input states comprising
  - (i) a first input state in said covering set, and
  - (ii) a second input state in said covering set,
  wherein, for any pair of output classes, said first input state and said second input state distinguish said pair of output classes, wherein said chosen network testing experiments comprise measured changes in one or more cellular constituents from the first input state to the second input state of each chosen pair of input states.

61. The method of claim 60 wherein said step of identifying a covering set of input states comprises determining a solution to a linear integer programming problem, wherein said linear integer programming problem comprises a pair of inequalities for each output class, said pair of inequalities consisting of:
- (i) a first inequality representing all input states in which output classes in a pair of output classes have different behaviors, and
- (ii) a second inequality representing all input states in which output classes in a pair of output classes have the same behavior.

62. The method of claim 61 wherein the solution to said linear integer programming problem is determined by means of a branch-and-bound algorithm.

63. The method of claim 61
wherein all input states in said covering set of input states are assigned individual experimental costs, and
wherein the solution to said linear integer programming problem minimizes the sum of individual experimental costs of all input states in said covering set of input states.

64. The method of claim 60 wherein said step of choosing pairs of input states comprises determining a solution to a linear integer programming problem, wherein said linear integer programming problem comprises an inequality for each possible pair of output classes, said inequality representing all pairs of input states in the covering set in which output classes in said pair of output classes have different behaviors.

65. The method of claim 64 wherein the solution to said linear integer programming problem is determined by means of a branch-and-bound algorithm.

* * * * *